US010189009B2

(12) United States Patent
Ueda et al.

(10) Patent No.: US 10,189,009 B2
(45) Date of Patent: Jan. 29, 2019

(54) PARTICULATE WATER ABSORBING AGENT AND METHOD FOR MANUFACTURING SAME

(71) Applicant: NIPPON SHOKUBAI CO., LTD., Osaka (JP)

(72) Inventors: Manabu Ueda, Himeji (JP); Takahiro Kitano, Himeji (JP); Yoshitaka Ikeuchi, Himeji (JP); Hiroyuki Ikeuchi, Himeji (JP); Katsuyuki Wada, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 172 days.

(21) Appl. No.: 14/424,315

(22) PCT Filed: Aug. 30, 2013

(86) PCT No.: PCT/JP2013/073433
§ 371 (c)(1),
(2) Date: Feb. 26, 2015

(87) PCT Pub. No.: WO2014/034897
PCT Pub. Date: Mar. 6, 2014

(65) Prior Publication Data
US 2015/0217270 A1    Aug. 6, 2015

(30) Foreign Application Priority Data

Aug. 30, 2012   (JP) ................. 2012-190325

(51) Int. Cl.
*B01J 20/28*     (2006.01)
*C08J 3/12*      (2006.01)
*C08J 3/24*      (2006.01)
*B01J 20/26*     (2006.01)
*B01J 20/30*     (2006.01)
*B01J 20/02*     (2006.01)
*B01J 20/10*     (2006.01)
*A61L 15/42*     (2006.01)
*A61L 15/60*     (2006.01)
*B01J 20/04*     (2006.01)
*B01J 20/12*     (2006.01)
*B01J 20/14*     (2006.01)
*B01J 20/18*     (2006.01)
*C08J 3/075*     (2006.01)
*C08K 3/34*      (2006.01)
*C08K 3/36*      (2006.01)
*C08K 3/30*      (2006.01)
*C08K 3/011*     (2018.01)

(52) U.S. Cl.
CPC ......... *B01J 20/28016* (2013.01); *A61L 15/42* (2013.01); *A61L 15/60* (2013.01); *B01J 20/02* (2013.01); *B01J 20/04* (2013.01); *B01J 20/041* (2013.01); *B01J 20/048* (2013.01); *B01J 20/10* (2013.01); *B01J 20/103* (2013.01); *B01J 20/12* (2013.01); *B01J 20/14* (2013.01); *B01J 20/18* (2013.01); *B01J 20/261* (2013.01); *B01J 20/264* (2013.01); *B01J 20/267* (2013.01); *B01J 20/28004* (2013.01); *B01J 20/28011* (2013.01); *B01J 20/3021* (2013.01); *B01J 20/3085* (2013.01); *C08J 3/075* (2013.01); *C08J 3/12* (2013.01); *C08J 3/245* (2013.01); *C08K 3/34* (2013.01); *B01J 2220/68* (2013.01); *C08J 2300/14* (2013.01); *C08J 2333/02* (2013.01); *C08K 3/011* (2018.01); *C08K 3/36* (2013.01); *C08K 2003/3081* (2013.01); *F04C 2270/041* (2013.01)

(58) Field of Classification Search
CPC .................................................. B01J 20/28016
See application file for complete search history.

(56) References Cited

U.S. PATENT DOCUMENTS

| | | |
|---|---|---|
| 6,150,582 A | 11/2000 | Wada et al. |
| 6,403,700 B1 | 6/2002 | Dahmen et al. |
| 6,605,673 B1 | 8/2003 | Mertens et al. |
| 6,930,221 B1 | 8/2005 | Strandqvist |
| 2002/0128618 A1 | 9/2002 | Frenz et al. |

(Continued)

FOREIGN PATENT DOCUMENTS

| | | |
|---|---|---|
| CA | 2433044 | 7/2002 |
| CN | 1747752 A | 3/2006 |

(Continued)

OTHER PUBLICATIONS

Chinese Office Action dated Nov. 4, 2015, issued in counterpart Patent Application No. 2013-80044978.1.
Japanese Office Action dated Sep. 13, 2016, issued in counterpart Patent Application No. 2014-533135.
International Preliminary Report on Patentability for PCT/JP2013/073433, dated Mar. 12, 2015.

(Continued)

*Primary Examiner* — Peter F Godenschwager
(74) *Attorney, Agent, or Firm* — Dickinson Wright PLLC

(57) ABSTRACT

A water absorbent resin (water absorbing agent) and method for producing it are provided which improve, in a water absorbent article (in particular, a diaper) including a water absorbent resin as a water absorbing agent, the absolute absorption amount (g), liquid absorbing times (in particular, liquid absorbing times at the second instance and later), re-wet (g), and diffusion distance (%) of the water absorbent article.
A particulate water absorbing agent of the present invention has a CRC, a proportion of particles with sizes of 600 μm to 150 μm as defined through a standard-sieve classification, an SST, and the value of the difference between an FST and the SST each within a predetermined range.

8 Claims, 1 Drawing Sheet

(56) References Cited

U.S. PATENT DOCUMENTS

| | | |
|---|---|---|
| 2004/0106745 A1 | 6/2004 | Nakashima et al. |
| 2005/0209352 A1 | 9/2005 | Dairoku et al. |
| 2006/0073969 A1 | 4/2006 | Torii et al. |
| 2006/0204755 A1 | 9/2006 | Torii et al. |
| 2007/0066167 A1 | 3/2007 | Wada et al. |
| 2007/0123658 A1* | 5/2007 | Torii ............ A61L 15/60 525/329.7 |
| 2007/0141338 A1 | 6/2007 | Ishizaki et al. |
| 2007/0244283 A1 | 10/2007 | Riegel et al. |
| 2008/0269372 A1 | 8/2008 | Dairoku et al. |
| 2009/0208748 A1 | 8/2009 | Torii et al. |
| 2009/0298685 A1 | 12/2009 | Torii et al. |
| 2010/0308263 A1 | 12/2010 | Torii et al. |
| 2013/0175473 A1 | 7/2013 | Wada et al. |

FOREIGN PATENT DOCUMENTS

| | | |
|---|---|---|
| CN | 1856331 A | 11/2006 |
| CN | 1917954 A | 2/2007 |
| EP | 0629411 | 12/1994 |
| EP | 1730218 | 12/2010 |
| JP | 10-147724 | 6/1998 |
| JP | 11-58615 | 3/1999 |
| JP | 2003-105092 | 4/2003 |
| JP | 2005-111474 | 4/2005 |
| JP | 2006-57075 | 3/2006 |
| JP | 2009-114391 | 5/2009 |
| JP | 2009-531158 A | 9/2009 |
| WO | 92/18171 | 10/1992 |
| WO | 95/22356 | 8/1995 |
| WO | 95/26209 | 10/1995 |
| WO | 98/48857 | 11/1998 |
| WO | 99/55767 | 11/1999 |
| WO | 01/66056 | 9/2001 |
| WO | 02/053199 | 7/2002 |
| WO | 2004/018005 | 3/2004 |
| WO | 2004/069915 | 8/2004 |
| WO | 2004/096304 | 11/2004 |
| WO | 2005/092955 | 10/2005 |
| WO | 2005/097881 | 10/2005 |
| WO | 2012/043821 | 4/2012 |

OTHER PUBLICATIONS

International Search Report for PCT/JP2013/073433, dated Dec. 3, 2013, and English translation thereof.

\* cited by examiner

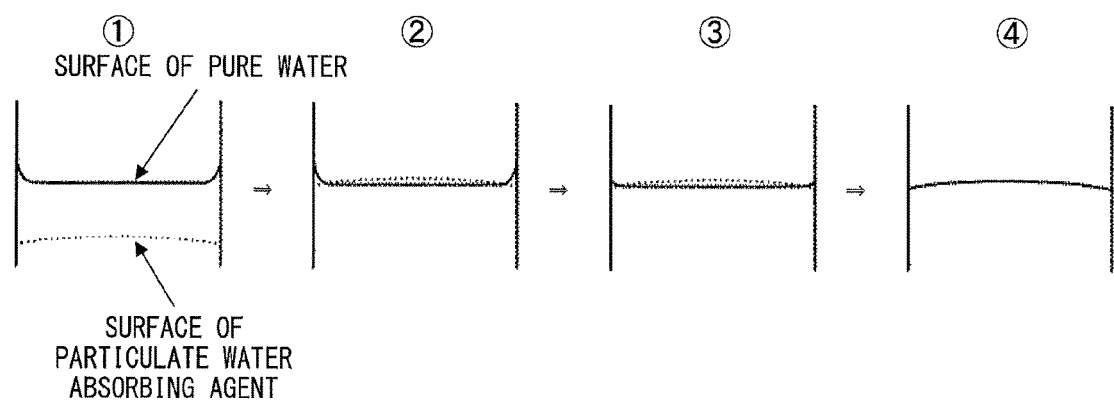

PARTICULATE WATER ABSORBING AGENT AND METHOD FOR MANUFACTURING SAME

TECHNICAL FIELD

The present invention relates to a particulate water absorbing agent containing a water absorbent resin as a main component and a method for producing the particulate water absorbing agent, and to a water absorbent article. More particularly, the present invention relates to (i) a particulate water absorbing agent suitably usable in sanitary materials such as a disposable diaper, a sanitary napkin, and an incontinence pad, and to (ii) a method for producing the particulate water absorbing agent.

BACKGROUND ART

Current sanitary materials (water absorbent articles) such as a disposable diaper, a sanitary napkin, and an incontinence pad typically include, as a constituent ingredient (water absorbing agent), a water absorbent resin and a hydrophilic fiber such as pulp to absorb body fluids.

Known examples of the water absorbent resin as a water absorbing agent include a crosslinked partially neutralized polyacrylic acid, a hydrolyzed starch-acrylonitrile graft polymer, a neutralized starch-acrylic acid graft polymer, a saponified vinyl acetate-acrylic ester copolymer, a crosslinked carboxymethyl cellulose, a hydrolyzed acrylonitrile copolymer or hydrolyzed acrylamide copolymer, a crosslinked acrylonitrile copolymer or crosslinked acrylamide copolymer, a crosslinked cationic monomer, a crosslinked isobutylene-maleic copolymer, a crosslinked polymer of 2-acrylamide-2-methylpropanesulfonate and acrylic acid and the like.

Recent years have seen a tendency toward an increase in (i) the amount (g) of use of a water absorbent resin in a single sanitary material such as a disposable diaper and a sanitary napkin and in (ii) the weight ratio (weight %) of a water absorbent resin relative to the entire absorbent body including the water absorbent resin, a hydrophilic fiber and the like. Specifically, (i) the amount of a hydrophilic fiber (pulp), which has a low bulk specific gravity, is reduced while (ii) the use amount of a water absorbent resin, which has an excellent water absorbency and a high bulk specific gravity, is increased for an increase in the proportion (weight %) of a water absorbent resin in an absorbent body. This intends to reduce the thickness of sanitary materials without decreasing the amount of water that the sanitary materials are capable of absorbing. This has in turn required a water absorbent resin, instead of a hydrophilic fiber such as pulp, to serve a function related to liquid transportation and allocation.

A gel of a water absorbent resin swollen in an absorbent body serves a transportation function with use of a capillary phenomenon through gaps between gel particles. It is typically presumed that a water absorbent resin with higher gel strength has higher transportability, while a water absorbent resin with lower gel strength has lower transportability, that is, lower diffusibility of liquid in an absorbent body, as a result of a so-called gel blocking phenomenon.

Typically, to have high gel strength in a swollen state, a polymer for the water absorbent resin should have a high degree of crosslinking. Such a high degree of crosslinking, however, inevitably leads to a decrease in the swelling capacity and retention ability. Patent Literature 1 discloses a method for improving the swelling pressure of a gel of a surface-crosslinked water absorbent resin produced through an acid-type polymerization at a low neutralization rate and subsequent neutralization. This method is, however, problematic in that, for example, it jeopardizes the safety in handling a polymer with high acidity and complicates the production process. The above method is therefore difficult to apply to industrial production.

A water absorbent resin may, as is well-known, be subjected to a surface treatment to have high gel strength. This technique causes a water absorbent resin to be treated with use of (i) any of various surface-crosslinking agents that can react with a carboxyl group in polymer molecules at the surface of the water absorbent resin or (ii) a particular polymer that can react as such, and thus intends to produce a water absorbent resin with high gel strength and high liquid-absorbing ability under pressure. The technique thereby prevents a gel blocking phenomenon.

Various attempts have been made at such surface treatments to modify the surface of a water absorbent resin for prevention of a gel blocking phenomenon. Known examples of such attempts include a method of using a water absorbent resin crosslinked with use of a particular metal ion (Patent Literatures 2 and 3), a method of modifying a water absorbent resin with use of a polyamine and polyimine in an organic solvent (Patent Literature 4), a method of surface-treating a water absorbent resin with use of a surface treatment agent containing a polyol and a cation in the state of an aqueous solution (Patent Literature 5), a method of surface-treating a water absorbent resin with use of (i) an organic crosslinked compound other than a polyol and (ii) a surface treatment agent containing a cation in the state of an aqueous solution (Patent Literature 5), and the like. Any of these publicly known methods may be used to prevent gel blocking.

The above publicly known methods, however, fail to ensure sufficient transportability of liquid in an absorbent body. Further, surface-crosslinking a water absorbent resin for increased gel strength increases the crosslinking density at the surface and its vicinity of the particles, so it fails to essentially improve the gel strength as the inside of the particles remains untreated.

There have already been particularly well-known attempts of adding, for example, an inorganic compound to a water absorbent resin to improve usability, preservability, or water-absorbing performance of a powder of the water absorbent resin. Known examples of such attempts include a method of dry-blending a polyhydric metal salt such as aluminum sulfate with a water absorbent resin and subsequently contacting the blended product with a binding agent (for example, water) to produce a water absorbent resin in which gel blocking does not easily occur (Patent Literature 6), a method of mixing in a Vortex mixer a water absorbent resin with a permeability retaining agent (for example, silica, alumina, titania, clay, an emulsified polymer, or a precipitated polymer) and subsequently applying mechanical stress to the mixture in, for example, an Osterizer blender (Patent Literature 7), a method of coating with a three-dimensional or electrostatic spacer a surface-crosslinked water absorbent resin having a particular gel strength (Patent Literature 8), a super water absorbent resin composition containing a fine powder of an aggregate of a hydrous oxide including a super water absorbent resin and two kinds of metals M1 and M2 each having a -M1-O-M2- bond as at least part thereof (Patent Literature 9), and the like.

While the above publicly known methods can prevent gel blocking, even the use of the above methods may fail to achieve sufficient transportability of liquid in a diaper. Even if the above methods achieve sufficient liquid transportability, they require an excessively large amount of a gel-blocking preventing agent such as organic or inorganic fine particles. The above methods thus pose such problems of dust as dusting, filter clogging, and the like in a production line for a water absorbing agent or a diaper. The above methods therefore leave room for improvement in terms of safety and cost.

There has also been proposed, as a method for improving the gel strength of a water absorbent resin while maintaining its swelling capacity and retention ability, a method of using a chain transfer agent in combination for polymerization and using a crosslinking agent in a large amount (Patent Literature 10). However, this method, which not only adds a chain transfer agent but also requires a crosslinking agent in an amount larger than normal, is disadvantageous in terms of cost.

Another known example of an index of the degree of gel blocking is saline flow conductivity (SFC) in Patent Literature 11. Examples of a method of adding inorganic fine particles to improve the SFC and other liquid permeabilities include the methods disclosed in Patent Literatures 12 to 17, etc. These evaluation methods, however, also fail to produce a water absorbent resin that achieves sufficient performance when used in a diaper.

Other known techniques for improving a water absorbent resin are (i) techniques in which the particle size of a main component is 600 to 150 μm (Patent Literatures 17 to 19) and techniques in which the particle size of a main component is 297 to 149 μm (Patent Literature 20).

The above methods have improved and dealt with such physical property values of a water absorbent resin as not only water absorption capacity (without load), water absorption capacity under load, water absorbing speed, and liquid permeability, but also particle size, moisture content, degree of coloration, and the like. There has been proposed a water absorbent resin of which the above physical property values are controlled. For example, as disclosed in Non Patent Literatures 1 to 7 listed below, physical property values such as water absorption capacity, water absorption capacity under load, and water absorbing speed are defined by, for example, the European Diaposables And Nonwovens Association (EDANA) and JIS (the JIS defines the water absorption capacity and water absorbing speed of a water absorbent polymer). Specifically, the water absorbing speed (typically the Vortex method or FFST method) is defined on the basis of the absorption time (seconds), that is, the time period necessary for a dry powder of a water absorbent resin to gelatinize a predetermined amount of liquid. Thus, the water absorbing speed is used to evaluate the behavior of a dry powder of a water absorbent resin.

As described above, although there have been proposed a lot of improvements for water absorbent resins, there is still room for improvement in the absorbing ability of a water absorbent resin in an absorbent article (for example, a diaper). Specifically, a diaper requires such properties as "absolute absorption amount (g)" (indicative of the absorbing ability of a single diaper). For an increasing in the "absolute absorption amount (g)", a water absorbent resin simply needs to have increased water absorption capacity (centrifuge retention capacity or CRC (g/g)). However, increasing the water absorption capacity (CRC) tends to, for the second and third instances of urine discharge in a diaper, decrease the "liquid absorbing time (in particular, a liquid absorbing time for the second time and thereafter) and also decrease the "diffusion distance (%)" (index of liquid diffusibility). In addition, increasing the "absolute absorption amount (g)" does not necessarily improve the "re-wet (g)" of a diaper.

CITATION LIST

Patent Literature 1
U.S. Pat. No. 6,403,700 (Patented Date: Jun. 11, 2002)
Patent Literature 2
U.S. Pat. No. 6,930,221 (Patented Date: Aug. 16, 2005)
Patent Literature 3
PCT International Publication No. 99/55767 Pamphlet (Publication Date: Nov. 4, 1999)
Patent Literature 4
PCT International Publication No. 95/22356 Pamphlet (Publication Date: Aug. 24, 1995)
Patent Literature 5
U.S. Pat. No. 6,605,673 (Patented Date: Aug. 12, 2003)
Patent Literature 6
PCT International Publication No. 98/48857 Pamphlet (Publication Date: Nov. 5, 1998)
Patent Literature 7
PCT International Publication 01/66056 Pamphlet (Publication Date: Sep. 13, 2001)
Patent Literature 8
US Patent Application Publication No. 2002/0128618 (Publication Date: Sep. 12, 2002)
Patent Literature 9
Japanese Patent Application Publication, Tokukaihei, No. 10-147724 (Publication Date: Jun. 2, 1998)
Patent Literature 10
US Patent Application Publication No. 2007/123658 (Publication Date: May 31, 2007)
Patent Literature 11
PCT International Publication No. 95/26209 Pamphlet (Publication Date: Oct. 5, 1995)
Patent Literature 12
PCT International Publication No. 2004/069915 Pamphlet (Publication Date: Aug. 19, 2004)
Patent Literature 13
PCT International Publication No. 2004/018005 Pamphlet (Publication Date: Mar. 4, 2004)
Patent Literature 14
PCT International Publication No. 2002/053199 Pamphlet (Publication Date: Jul. 11, 2002)
Patent Literature 15
Japanese Patent Application Publication, Tokukai, No. 2009-114391 (Publication Date: May 28, 2009)
Patent Literature 16
PCT International Publication No. 2004/096304 Pamphlet (Publication Date: Nov. 11, 2004)
Patent Literature 17
PCT International Publication No. 2005/097881 Pamphlet (Publication Date: Oct. 20, 2005)
Patent Literature 18
European Patent Publication No. 0629411 (Publication Date: Dec. 21, 1994)
Patent Literature 19
European Patent Publication No. 1730218 (Publication Date: Dec. 13, 2006)
Patent Literature 20
PCT International Publication No. 92/18171 Pamphlet (Publication Date: Oct. 29, 1992)
Non Patent Literature 1
CRC (Centrifuge Retention Capacity) (ERT 441.2-02 (2002))

Non Patent Literature 2
AAP (Absorption Against Pressure) (ERT 442.2-02)
   Non Patent Literature 3
Extractables (ERT 470.2-02 (2002))
   Non Patent Literature 4
Residual Monomers (ERT 410.2-02 (2002))
   Non Patent Literature 5
Particle Size DiFST ibution (ERT 420.2-02 (2002))
   Non Patent Literature 6
JIS K7224:1996, Testing Method for Water Absorbing Speed of Super Absorbent Polymers
   Non Patent Literature 7
JIS K7223:1996, Testing Method for Water Absorption Capacity of Super Absorbent Polymers

SUMMARY OF INVENTION

Technical Problem

As described above, although there have been proposed a lot of improvements for water absorbent resins, there is still room for improvement in the absorbing ability of a water absorbent resin in a water absorbent article (for example, a diaper). It is an object of the present invention to provide (i) a particulate water absorbing agent for use in a water absorbent article (in particular, a diaper) including a water absorbent resin as a water absorbing agent, the particulate water absorbing agent improving the "absolute absorption amount (g)", "liquid absorbing time (in seconds: in particular, a liquid absorbing time for the second instance and thereafter", "re-wet (g)", and "diffusion distance (%)" of that water absorbent article, and (ii) a method for producing the particulate water absorbing agent.

Solution to Problem

The inventors of the present invention have conducted diligent studies to solve the above problem, and have thus found out the following: Although there have been proposed many parameters, most of those parameters are related to water absorption behavior (for example, water absorption, liquid permeation, gel strength, and durability) exhibited when a dry water absorbent resin powder is gelatinized with a predetermined amount of liquid such as physiological saline and synthesized urine. Such efforts have thus failed to sufficiently contribute to the absorbing ability of a water absorbent article (for example, a diaper). The inventors of the present invention have studied the cause of the failure, and have thus discovered that conventional methods for evaluating a water absorbing speed (based on the time needed for a dry water absorbent resin powder to gelatinize a predetermined amount of liquid; first-instance pure-water 50-fold swelling time (first swelling time or FST)) are not sufficiently correlated to the water absorbent property of a diaper.

The inventors of the present invention have, to solve the above problem, studied conventional methods for evaluating the water absorbing speed and water absorption capacity (based on the time needed for a dry water absorbent resin powder to gelatinize a predetermined amount of liquid and the ability of such a dry water absorbent resin powder to gelatinize a predetermined amount of liquid), and have thus discovered that a large decrease of the second-instance pure-water 50-fold swelling time (herein referred to also as "second swelling time" or "SST") (for a hydrogel swollen once to further absorb water) over the FST leads to decreased properties of a particulate water absorbing agent when the particulate water absorbing agent is actually used in a diaper.

The inventors of the present invention have then discovered that to solve the above problem (that is, to improve the absolute absorption amount, liquid absorbing times, re-wet, and diffusion distance of a diaper), it is important for a particulate water absorbing agent to have a certain water absorption capacity (CRC≥32) or higher and a particular particle size (particles with sizes of 600 μm to 150 μm as defined through a standard-sieve classification account for 80 mass % or more), and it is also important that as had not been considered, the second-instance pure-water 50-fold swelling time (SST) be short and that the difference (hereinafter referred to also as "DST (difference swelling time)" calculated by SST−FST) between the first-instance pure-water 50-fold swelling time (FST) and the second-instance pure-water 50-fold swelling time (SST) be small. The inventors of the present invention have discovered that a particulate water absorbing agent that satisfies the above conditions would uniquely solve the above problem, and have thereby completed the present invention.

Specifically, to solve the above problem, the present invention provides a particulate water absorbing agent including: a polyacrylic acid (salt)-based water absorbent resin as a main component, the particulate water absorbing agent having a swelling rate (CRC) of 32 g/g to 45 g/g relative to 0.9-mass % saline, the particulate water absorbing agent including, at a proportion of 80 mass % or more, a particle having a size of 600 μm to 150 μm as defined through a standard-sieve classification, the particulate water absorbing agent having a second-instance pure-water 50-fold swelling time (SST (in seconds)) of 70 seconds or less, a difference (DST=SST−FST) between a first-instance pure-water 50-fold swelling time (FST (in seconds)) and the second-instance pure-water 50-fold swelling time (SST (in seconds)) being +10 seconds or less.

To solve the above problem, the present invention provides a method for producing a water absorbing agent, the method including the steps of: (1) polymerizing a monomer aqueous solution including acrylic acid (salt) as a main component, the monomer aqueous solution having a monomer concentration of 30 mass % or more, the polymerization involving use of an internal crosslinking agent in an amount of 0.04 mol % or more relative to the monomer and producing a hydrogel; (2) drying the hydrogel, produced through the step (1), to produce a dried product having a swelling rate (CRC) of 35 g/g to 55 g/g; (3) pulverizing the dried product into particles and optionally classifying the particles to produce a water absorbent resin powder including, at 80 mass % or more relative to the entire water absorbent resin powder, a particle having a size of 600 μm to 150 μm as defined through a standard-sieve classification; (4) adding a surface-crosslinking agent, which includes a compound containing a hydroxyl group and/or a derivative group thereof, to the water absorbent resin powder, produced through the step (3), to decrease the swelling rate (CRC) by 3 g/g to 15 g/g to a swelling rate (CRC) of 32 g/g to 50 g/g to produce a surface-crosslinked water absorbent resin powder; and (5) adding a liquid permeability improving agent to the water absorbent resin powder simultaneously with and/or after the step (4).

In particular, the DST (the second-instance pure-water 50-fold swelling time (SST) minus the first-instance pure-water 50-fold swelling time (FST)) of the particulate water absorbing agent being +10 seconds or less means that the water absorbing speed at the second instance is higher than that at the first instance or that the water absorbing speed at the first instance and that at the second instance are equivalent to each other (Measurements of the water absorbing speed are described in detail in the Examples below). The DST is a numerical representation of the difference between the first swelling time and the second swelling time, which is for a particulate water absorbing agent having absorbed liquid once and being in the form of a gel layer. The particulate water absorbing agent of the present invention characteristically has a DST of +10 seconds or less, preferably within the range specified under (DST) below, for example, a DST of 0 seconds or less.

Specifically, the water absorbing agent of the present invention is capable of exhibiting a sufficient liquid-absorbing ability (liquid transportability) even after absorbing liquid once, that is, after the second instance and later. The particulate water absorbing agent of the present invention is, in other words, capable of producing a sufficient gel-blocking preventing effect.

Further, the particulate water absorbing agent has a water absorption capacity of 32 g/g or more and contains, at 80 mass % or more, particles with sizes of 600 μm to 150 μm as defined through a standard-sieve classification. The particulate water absorbing agent thus has a large surface area. This indicates that the particulate water absorbing agent of the present invention is excellent in liquid transportability (capillary force) expressed between gel particles when the water absorbing agent is swollen.

The above novel production method, which is an example method for producing the above novel particulate water absorbing agent, allows production of a water absorbent article that has an excellent gel property and that, in the case where it is used as a disposable diaper, a sanitary napkin or the like, exhibits excellent physical properties that were previously unachievable.

Advantageous Effects of Invention

The present invention provides a novel particulate water absorbing agent that has an excellent gel property and that, in the case where it is used in an absorbent body for a sanitary material such as a disposable diaper, exhibits excellent physical properties. The present invention further provides a method for producing a particulate water absorbing agent that has an excellent gel property and that, in the case where it is used in an absorbent body for a sanitary material such as a disposable diaper, exhibits excellent physical properties.

BRIEF DESCRIPTION OF DRAWINGS

FIG. 1 shows diagrams schematically illustrating how to determine the end point (end time point) of a measurement of a first-instance pure-water 50-fold swelling time (FST (in seconds)) and second-instance pure-water 50-fold swelling time (SST (in seconds)). In FIG. 1, diagram 1 illustrates how the particulate water absorbing agent is swollen with its surface rising, diagram 2 illustrates the particulate water absorbing agent having a surface that has risen beyond the surface of the pure water, diagram 3 illustrates how pure water raised at the wall surface by surface tension is absorbed, and diagram 4 illustrates the surface of the pure water having been replaced with the surface of the particulate water absorbing agent.

DESCRIPTION OF EMBODIMENTS

The description below deals in detail with an embodiment of the present invention. In the present specification, the expression "A to B" indicative of a range is intended to mean "not less than A and not greater than B". Further, all the patent and non-patent documents cited in the present specification are incorporated in the present specification by reference.

The present invention regards weight and mass as similar in meaning, and also regards weight % and mass % as similar in meaning. The present specification uses "mass" and "mass %" only.

The description below deals in detail with the present invention by sequentially discussing the definitions of terms under item (A), a method of the present invention for producing a particulate water absorbing agent under item (B), a particulate water absorbing agent of the present invention under item (C), an absorbent body (water absorbent article) including a particulate water absorbing agent of the present invention under item (D), and other applications under item (E).

(A) DEFINITIONS OF TERMS

The description below first deals with "first-instance pure-water 50-fold swelling time (FST)" and "second-instance pure-water 50-fold swelling time (SST)" defined for the present invention.

[First-Instance Pure-Water 50-Fold Swelling Time (First Swelling Time or FST)]

The first-instance pure-water 50-fold swelling time (FST) indicates a swelling time of the particulate water absorbing agent relative to pure water.

The term "pure water" as used herein includes ultrapure water in its concept. The present invention uses water having an electric conductivity (at 25° C.) of 1.0 to 0.0548 S/cm or 1.0 to 0.1 μS/cm. The present invention uses, for example, ion-exchange water, reverse osmotic water, or distilled water each exhibiting the above electric conductivity. In particular, the present invention uses ion-exchange water exhibiting the above electric conductivity. The water having an electric conductivity within the above range (that is, the pure water for use in the present invention) is typically prepared by (i) filtering water (for example, tap water) with use of a filter or activated carbon as necessary, (ii) decarboxylating or deaerating the water, and (iii) either passing the water through an ion-exchange membrane or reverse osmosis membrane or subjecting the water to distillation.

A particulate water absorbing agent (0.200 g) at room temperature (25° C.±1° C.) is put into a test tube 1 (with an inner diameter of 14 mm, a height of 125 mm, and a thickness of 1 mm) in such a manner as not to adhere to the wall surface. The test tube 1 is fixed vertically. Next, 10.0 g of pure water is put into a test tube 2 of the same type and controlled to keep at 25° C.±1° C. This pure water is poured into the test tube 1 (which contains the particulate water absorbing agent) over a period of 2 to 3 seconds. The time point at which the pure water starts to be poured is referred to herein as "start time point 1".

Then, a measurer or measurement camera is let stand in such a manner that a central portion of an eyeball or lens of the measurement camera is positioned at a horizontal distance of 18 to 22 cm from the test tube 1 and above the liquid surface of the pure water in the test tube 1 at an angle of 18° to 22° to the liquid surface (6 to 9 cm above the liquid surface). The term "horizontal distance" as used herein refers to a horizontal distance extending from a central portion of an eyeball of the measurer or lens of the measurement camera to the outside wall of the test tube 1.

Observation from the above position confirms that the liquid surface of the pure water is replaced with a swollen particulate water absorbing agent (that is, pure water raised at the wall surface by surface tension is fully absorbed) at a time point. This time point is referred to herein as "end time point 1". (See FIG. 1 for how to determine the end point.)

FIG. 1 shows diagrams schematically illustrating how to determine the end point (end time point) of a measurement of a first-instance pure-water 50-fold swelling time (FST (in seconds)) and second-instance pure-water 50-fold swelling time (SST (in seconds)) described below. In FIG. 1, diagram 1 illustrates how the particulate water absorbing agent is swollen with its surface rising, diagram 2 illustrates the particulate water absorbing agent having a surface that has risen beyond the surface of the pure water, diagram 3 illustrates how pure water raised at the wall surface by surface tension is absorbed, and diagram 4 illustrates the surface of the pure water having been replaced with the surface of the particulate water absorbing agent.

The FST is a value expressed in seconds to indicate the difference between the end time point 1 and the start time point 1 (that is, the end time point 1 minus the start time point 1), the value being rounded off to the nearest whole number. The FST is a mean value (rounded off to the nearest whole number) of three measurements.

[Second-Instance Pure-Water 50-Fold Swelling Time (Second Swelling Time or SST)]

The second-instance pure-water 50-fold swelling time (SST) indicates a swelling time of the particulate water absorbing agent at the second instance after the particulate water absorbing agent is swollen once with pure water.

Ten minutes after the start time point 1, 10.0 g of pure water is poured into the test tube 1, which contains the swollen particulate water absorbing agent from the FST measurements, in a manner similar to the manner for the FST measurements. The time point at which the pure water starts to be poured for the second instance (that is, 10 minutes after the start time point 1) is referred to herein as "start time point 2".

The end time point 2 is determined in a manner similar to the manner for the FST measurements. The SST is a value expressed in seconds to indicate the difference between the end time point 2 and the start time point 2 (that is, the end time point 2 minus the start time point 2), the value being rounded off to the nearest whole number. The SST is a mean value (rounded off to the nearest whole number) of three measurements.

The DST (difference swelling time) is the difference between the FST and the SST. A DST of +10 seconds or less indicates that the particulate water absorbing agent has sufficient liquid-absorbing ability (liquid transportability) even at the second instance of water absorption and has an excellent gel-blocking preventing property. The DST is a mean value (rounded off to the nearest whole number) of the respective DST values of three measurements.

[Particulate Water Absorbing Agent]

The term "water absorbing agent" as used in the present specification refers to a gelatinizer that contains a water absorbent resin as a main component and that absorbs a water-based liquid. The term "particulate water absorbing agent" as used in the present specification refers to a water absorbing agent in the form of particles (powder). The present specification uses the term "particulate water absorbing agent" regardless of whether it refers to a single particle of the water absorbing agent or an aggregate of a plurality of particles of the water absorbing agent. The term "particulate" means having the form of particles. A particle is a small grain-shaped solid or liquid object with a measurable size (according to the Glossary of Technical Terms in Japanese Industrial Standards, fourth edition, page 2002). The present specification may refer to a particulate water absorbing agent simply as "water absorbing agent".

The water-based liquid for the present embodiment is not limited to water. Examples of the water-based liquid include urine, blood, sweat, feces, waste fluid, moisture, vapor, ice, a mixture of water and an organic and/or inorganic solvent, rain water, ground water, and the like. The water-based liquid is thus not limited in any particular manner as long as it contains water. Preferable examples include urine, menstrual blood, sweat, and other body fluids.

The particulate water absorbing agent of the present invention is suitably used in a sanitary material for absorbing a water-based liquid. The particulate water absorbing agent contains, as a main component, the water absorbent resin as a polymer. Specifically, the particulate water absorbing agent contains the water absorbent resin in an amount of preferably 60 to 100 mass %, 70 to 100 mass %, 80 to 100 mass %, or 90 to 100 mass %. The particulate water absorbing agent optionally further contains water as a non-polymer and/or an additive described in (6) under item (B) described below. A suitable moisture content (0.2 to 30 mass %) for the particulate water absorbing agent will be described later. The particulate water absorbing agent covers in scope a water absorbent resin composition made of the above components.

The water absorbing agent contains the water absorbent resin in an amount of up to approximately 99 mass %, more preferably 97 mass %, particularly preferably 95 mass %. The water absorbing agent preferably further contains water and/or an additive (inorganic fine particles or polyhydric metal cations) described later.

(B) Water absorbent resin contained in a particulate water absorbing agent of the present invention and a method of the present invention for producing a particulate water absorbing agent A method of the present invention for producing a particulate water absorbing agent is a method for producing a particulate water absorbing agent which method includes (1) a step of polymerizing a monomer aqueous solution containing acrylic acid (salt) as a main component, (2) a drying step, (3) either a pulverization step or a combination of a pulverization step and a classification step (or (3-2) particle size control through reverse phase suspension polymerization or spray polymerization, the control optionally involving pulverization), (4) a surface crosslinking step, and (5) a liquid permeability improving agent adding step. The description below deals with these steps one by one.

(1) Polymerization Step

The present embodiment essentially uses, as its particulate water absorbing agent, a particulate water absorbing agent containing a water absorbent resin that is produced by polymerizing a water-soluble unsaturated monomer and that has an internal crosslinked structure. The present embodiment preferably uses, as the water absorbent resin, a polycarboxylic acid-based water absorbent resin, which is, for example, one or a combination of two or more of a polyacrylic acid partially neutralized polymer, a hydrolyzed starch-acrylonitrile graft polymer, a starch-acrylic acid graft polymer, a saponified vinyl acetate-acrylic ester copolymer, a hydrolyzed acrylonitrile copolymer or hydrolyzed acrylamide copolymer, a crosslinked acrylonitrile copolymer or crosslinked acrylamide copolymer, a denatured crosslinked polyvinyl alcohol containing a carboxyl group, a crosslinked isobutylene-maleic anhydride copolymer, and the like.

The present embodiment preferably uses a polyacrylic acid (partially) neutralized polymer (also known as a polyacrylate-based water absorbent resin), which is produced by polymerizing and crosslinking a monomer containing acrylic acid and/or salt thereof (neutralized product) as a main component.

The polymerization step of the method of the present invention for producing a particulate water absorbing agent is characteristically performed with (i) the concentration of a monomer in an aqueous solution (concentration of a monomer in a monomer aqueous solution) being 30 mass % or more and (ii) the amount of an internal crosslinking agent being 0.04 mol % or more relative to the monomer. In terms of method, the polymerization is preferably aqueous solution polymerization, but may be reverse phase suspension polymerization. The description below deals with aqueous solution polymerization.

The monomer or even the polymer (polyacrylic acid) contains an acid group having a neutralization rate of preferably 10 to 100 mol %, more preferably 40 to 90 mol %, still more preferably 50 to 85 mol %, particularly preferably 60 to 75 mol %.

In the case where the monomer contains acrylic acid and/or salt thereof as a main component (preferably 50 mol % or more of the entire monomer), the monomer may optionally contain 0 to 30 mass % of a graft polymer component (for example, one or more kinds of graft polymer components selected from the group consisting of polyvinyl alcohol, starch, and cellulose), and further be used in combination with another monomer.

The monomer for such combinational use is one or more kinds of monomers selected from, for example, water-soluble or hydrophobic unsaturated monomers such as methacrylic acid, maleic acid (anhydride), fumaric acid, crotonic acid, itaconic acid, vinyl sulfonic acid, 2-(meth)acrylamide-2-methylpropanesulfonic acid, (meth)acryloxyalkane sulfonic acid, an alkali metal salt of (meth)acryloxyalkane sulfonic acid, an ammonium salt of (meth)acryloxyalkane sulfonic acid, N-vinyl-2-pyrrolidone, N-vinyl acetamide, (meth)acrylamide, N-isopropyl (meth)acrylamide, N,N-dimethyl (meth)acrylamide, 2-hydroxyethyl (meth)acrylate, methoxy polyethyleneglycol (meth)acrylate, polyethyleneglycol (meth)acrylate, isobutylene, and lauryl (meth)acrylate. Also, the monomer for combinational use may include a copolymerization component.

In the case where the present embodiment uses a monomer other than acrylic acid (salt) (that is, acrylic acid and/or salt thereof), such a monomer other than acrylic acid (salt) is contained in an amount of preferably 0 to 30 mol %, more preferably 0 to 10 mol %, relative to the total amount of acrylic acid and/or salt thereof as a main component.

The water absorbent resin essentially has a crosslinked structure. The water absorbent resin may be self-crosslinked (requiring no crosslinking agent), but is more preferably produced by copolymerizing or reacting the monomer as a main component with a crosslinking agent (internal crosslinking agent for the water absorbent resin) containing within an individual molecule two or more polymerizable unsaturated groups and/or two or more reactive groups.

Specific examples of the internal crosslinking agent include N,N'-methylene bis(meth)acrylamide, (poly)ethylene glycol di(meth)acrylate, (poly)propylene glycol di(meth)acrylate, trimethylolpropane di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallyl amine, poly(meth)allyloxyalkane, (poly)ethyleneglycol diglycidyl ether, glycerol diglycidyl ether, ethylene glycol, polyethyleneglycol, propylene glycol, glycerin, pentaerythritol, ethylenediamine, ethylene carbonate, propylene carbonate, polyethylene imine, glycidyl (meth)acrylate, and the like.

Any of the above internal crosslinking agents may be used alone, or two or more kinds of the above internal crosslinking agents may be mixed for use as appropriate. The internal crosslinking agent may be added to a reaction system at once or in portions. In the case where the present embodiment uses at least one kind or two or more kinds of internal crosslinking agents, the present embodiment preferably essentially uses a compound with two or more polymerizable unsaturated groups for polymerization in view of, for example, an absorbent property for a water absorbent resin or water absorbing agent as a final product.

The internal crosslinking agent is used in an amount of normally 0.04 mol % or more, preferably 0.04 to 2 mol %, more preferably 0.04 to 0.5 mol %, still more preferably 0.04 to 0.1 mol %, particularly preferably 0.04 to 0.07 mol %, relative to the monomer (excluding the crosslinking agent). In the case where the internal crosslinking agent is used in an amount of smaller 0.04 mol % (in particular, smaller than 0.001 mol %) or larger than 2 mol %, it may be impossible to produce a water absorbing agent that the present invention intends to produce.

In the case where the internal crosslinking agent is used to allow the polymer to have an internal crosslinked structure, the internal crosslinking agent simply needs to be added to the reaction system before, during, or after the polymerization of the monomer or after neutralization of the monomer. Whether the water absorbent resin has a crosslinked structure can be determined on the basis of whether it contains extractables (water-soluble content) in an amount with a value for "water-insoluble" as defined in Non Patent Literature 3 (ERT 470.2-02). In the case where the water absorbent resin contains extractables in an amount of 50 mass % or less, it is regarded as water-insoluble, that is, having a crosslinked structure. The water absorbent resin contains extractables in an amount of preferably 25 mass % or less, more preferably 20 mass % or less, still more preferably 15 mass % or less, particularly preferably 10 mass % or less. The lower limit is preferably as low as possible (0 mass %). It is, however, 1 mass % or approximately 2 mass % for a balance with the CRC.

The monomer can be polymerized through bulk polymerization or precipitation polymerization for production of a water absorbent resin for use in the present embodiment. In view of not only performance and ease of control of the polymerization but also an absorbent property of the swollen gel, the monomer is preferably polymerized through a method in which the monomer is in the form of an aqueous solution, the method being, for example, spray polymerization, drop polymerization, aqueous solution polymerization, or reverse phase suspension polymerization, in particular, aqueous solution polymerization or reverse phase suspension polymerization, more preferably aqueous solution polymerization. Examples of aqueous solution polymerization include (i) a method of polymerizing in a double-arm kneader the monomer in the form of an aqueous solution and crushing the resulting hydrogel while polymerizing a remaining portion of the monomer and (ii) a method of feeding the monomer in the form of an aqueous solution into a predetermined container or onto a belt being driven, boil the monomer for polymerization, and pulverizing the resulting gel with use of a meat chopper or the like.

In the case where the monomer is in the form of an aqueous solution, the aqueous solution (hereinafter referred to as "monomer aqueous solution") has a monomer concentration that is determined on the basis of the temperature of the aqueous solution and/or the kind of the monomer. The monomer concentration is thus not limited to any particular value. The monomer concentration of the aqueous solution during the polymerization step is within a range of preferably 30 mass % or more, more preferably 30 to 70 mass %, even more preferably 30 to 60 mass % or even 30 to 50 mass %. A monomer concentration of the aqueous solution outside the above range (for example, a monomer concentration of less than 30 mass %) may not allow the present invention to produce an intended water absorbing agent.

In the case where the monomer is used in the form of an aqueous solution for polymerization, in particular for aqueous solution polymerization, the monomer may be used in combination with a solvent other than water as necessary. Such a solvent for the combinational use is not limited to any particular kind.

Reverse phase suspension polymerization is a polymerization method involving a monomer aqueous solution suspended in a hydrophobic organic solvent, and is described in, for example, U.S. Pat. Nos. 4,093,776, 4,367,323, 4,446,261, 4,683,274, and 5,244,735. Aqueous solution polymerization is a method of polymerizing a monomer aqueous solution without use of a dispersion solvent, and is described in, for example, U.S. Pat. Nos. 4,625,001, 4,873,299, 4,286,082, 4,973,632, 4,985,518, 5,124,416, 5,250,640, 5,264,495, 5,145,906, and 5,380,808 and European patents Nos. 0811636, 0955086, and 0922717. The present embodiment can also use, for example, (i) monomers and initiators mentioned as examples for the above polymerization methods and (ii) methods for subsequent drying.

The above polymerization is initiated with use of a polymerization initiator, which is not limited to any particular one. Examples of the polymerization initiator include a pyrolytic initiator (for example, a persulfate such as sodium persulfate, potassium persulfate, and ammonium persulfate, a peroxide such as hydrogen peroxide, t-butyl peroxide, and methyl-ethyl-ketone peroxide, or an azo compound such as azonitrile compound, azoamidin compound, cyclic azoamidin compound, azoamide compound, alkyl azo compound, and 2,2'-azobis(2-amidinopropane)dihydro chloride), a photolytic initiator (for example, a benzoin derivative, a benzyl derivative, an acetophenone derivative, a benzophenone derivative, and an azo compound), and the like.

The present embodiment can further use, in combination with the polymerization initiator, a reducing agent for facilitating decomposition of the polymerization initiator to allow the combination to serve as a redox initiator. Examples of the reducing agent include a (bi)sulfite (salt) such as sodium sulfite and sodium hydrogen sulfite, a reducing metal (salt) such as L-ascorbic acid (salt) and ferrous salt, an amine, and the like. The reducing agent is, however, not limited to any particular one.

The present invention suitably uses aqueous solution polymerization. In the case where the aqueous solution polymerization is, for instance, heat-removing polymerization involving use of a double-arm kneader etc., the present embodiment desirably uses a pyrolytic initiator together with a reducing agent so that they serve as a redox initiator. Further, the present embodiment desirably uses a pyrolytic initiator in the case where the present embodiment feeds the monomer in the form of an aqueous solution into a predetermined container or onto a belt being driven for boiling polymerization (which undergoes a temperature not lower than the boiling point of water as a solvent).

The polymerization initiator is contained in an amount of normally 0.001 to 2 mol %, preferably 0.01 to 0.1 mol %, relative to the monomer. Containing the polymerization initiator in an amount of less than 0.001 mol % is not preferable because it lets a large amount of the monomer remain unreacted, with the result that a large amount of the monomer remains in a water absorbent resin or water absorbing agent to be produced. Containing the polymerization initiator in an amount of more than 2 mol % may be not preferable because it increases the amount of a water soluble component in a water absorbent resin or water absorbing agent to be produced.

(2) Drying Step

The method of the present invention for producing a water absorbing agent is preferably a drying step of producing, from the hydrogel produced through the polymerization step described above under (1), a dried product having a swelling rate (CRC) of 35 to 55 g/g. The water absorption capacity of the dried product can be adjusted by adjusting the amount and concentration of the crosslinking agent during the polymerization step and/or the temperature at which the hydrogel is heated for drying. In particular, the method preferably includes (i) polymerizing the monomer with use of the above amount (preferably 0.04 mol % or more) of the crosslinking agent for relatively high crosslinking and further (ii) heating the resulting hydrogel to dry it in order to improve the water absorption capacity so that the water absorption capacity is within a target range.

Specifically, the method typically (i) produces a water-containing gel-like crosslinked polymer through the polymerization, (ii) heats the water-containing gel-like crosslinked polymer to dry it so that it has a relatively low water absorption capacity (for example, a CRC of 10 to 35 g/g relative to the polymer solid content), and typically (iii) pulverizes the water-containing gel-like crosslinked polymer before and/or after the drying to finally produce a water absorbent resin having a water absorption capacity of 35 to 55 g/g. The method performs the drying through a method involving, for example, azeotropic dehydration or hot air at a temperature within a range of typically 60° C. to 250° C., preferably 100° C. to 220° C., more preferably 120° C. to 200° C. The heating for the drying within the above range is performed for a drying time period that depends on (i) the surface area of the polymer, (ii) the moisture content of the polymer, and (iii) the type of the dryer to be used, each of which may simply be so selected that a water absorbent resin as a final product will have an intended moisture content and an intended water absorption capacity (CRC), for example. The drying time period is, for example, within a range of 0.1 to 2 hours, or 0.2 to 1 hour.

The water absorbent resin (or water absorbing agent) usable for the present embodiment may contain any amount of moisture (water content of the water absorbent resin or water absorbing agent; measured on the basis of a drying loss caused by drying 1 g of the water absorbent resin at 180° C. for 3 hours). The water absorbent resin is, in view of physical properties of the water absorbing agent to be produced, in the form of a powder that exhibits fluidity even at room temperature. The water absorbent resin is in the form of a powder having a moisture content of more preferably 0.2 to 30 mass %, still more preferably 0.3 to 15 mass %, particularly preferably 0.5 to 10 mass %. The particulate water absorbing agent of the present invention preferably has a moisture content similar to the above moisture content.

A later description will deal with a particle diameter preferable for the water absorbent resin (water absorbing agent). A moisture content of not less than a predetermined value allows a powder of the water absorbent resin to have improved impact resistance. An excessively high moisture content will result in lower water-absorbing performance.

(3) Pulverization Step; or Pulverization Step and Classification Step

The method of the present invention for producing a water absorbing agent includes a pulverization step; or a pulverization step and classification step. The method, in other words, includes (i) a pulverization step of pulverizing the dried product, produced through the drying step described under (2) above, to produce a powder of the water absorbent resin and preferably further includes (ii) a classification step of classifying particles of the water absorbent resin powder produced through the pulverization step. Through the step(s), the method allows the water absorbent resin to include, before surface crosslinking, particles with sizes of 600 to 150 μm (as defined through a standard-sieve classification) in an amount of 80 mass % or more, preferably 85 mass % or more, more preferably 90 mass % or more, particularly preferably 92 mass % or more (the upper limit being 100 mass %) relative to the entire water absorbent resin powder.

The pulverization step is a step of pulverizing the dried product to produce a powder of the water absorbent resin. The classification step is a step of classifying particles of the water absorbent resin powder produced through the pulverization step.

The classification step may be omitted in the case where the water absorbent resin powder produced through the pulverization step includes particles with sizes of 600 μm to 150 μm as defined through a standard-sieve classification in an amount of 80 mass % or more relative to the entire water absorbent resin powder.

If the water absorbent resin powder produced through the pulverization step does not include particles with sizes of 600 μm to 150 μm as defined through a standard-sieve classification in an amount of 80 mass % or more relative to the entire water absorbent resin powder, the classification step may simply be further performed so that the water absorbent resin powder produced through the classification step includes particles with sizes of 600 μm to 150 μm as defined through a standard-sieve classification in an amount of 80 mass % or more relative to the entire water absorbent resin powder.

The expression "particles with sizes of 600 μm to 150 μm as defined through a standard-sieve classification" in the present specification refers to particles that pass through a JIS standard sieve (JIS Z8801-1 (2000)) having a mesh size of 600 μm and that remain on a JIS standard sieve having a mesh size of 150 μm.

The expression "water absorbent resin powder including particles with sizes of 600 μm to 150 μm as defined through a standard-sieve classification in an amount of 80 mass % or more relative to the entire water absorbent resin powder" in the present specification means that particles that pass through a JIS standard sieve having a mesh size of 600 μm and that remain on a JIS standard sieve having a mesh size of 150 μm account for 80 mass % or more of the mass of water absorbent resin powder having undergone the pulverization step (or pulverization step and classification step).

The pulverization step can be performed by, for example, pulverizing, with use of a pulverizer, the dried product produced through the drying step. The pulverizer is not limited to any particular one. Examples of the pulverizer include a roll-type pulverizer such as a roll mill, a hammer-type pulverizer such as a hammer mill, an impact-type pulverizer, a cutter mill, a turbo grinder, a ball mill, a flash mill, and the like. The pulverization step more preferably uses a roll mill among others to control the particle size distribution.

The classification step may be performed by (i) classifying, with use of a sieve having a particular mesh size, particles of the water absorbent resin powder, as pulverized through the above step, to control the particle size distribution of the water absorbent resin powder so that it is a particular particle size distribution and thereby (ii) removing any particle having a particle diameter larger than a particular particle diameter. Such removed particles may be pulverized again to control the particle size distribution of the water absorbent resin powder so that it is within a particular particle diameter range.

The sieve classification can involve any classification device. Examples of the classification device include a vibrating sieve (for example, of an unbalanced weight driving type, a resonance type, a vibrating motor type, an electromagnetic type, or a circular vibrating type), an in-plane motion sieve (for example, of a horizontal motion type, a horizontal circular-linear motion type, or a three-dimensional circular motion type), a movable net type sieve, a forced stirring type sieve, a mesh surface vibrating type sieve, a wind power sieve, a sound wave sieve, and the like. The classification device is more preferably a vibrating sieve or an in-plane motion sieve.

Such a particle size control can be performed through not only a particle diameter control performed during the polymerization as necessary but also (i) the pulverization step, the classification step, and a blending step (of mixing particles for a predetermined particle size distribution) after the classification as well as (ii) as necessary, a granulating step (of binding a plurality of particles to form larger particles) and a fine powder recycling step (that is, a step of reusing, in the steps before the classification step (for example, the polymerization step and the drying step), fine powder produced through the classification, for example, particles having passed through a 150-μm mesh (fine powder having passed through a JIS standard sieve having a mesh size of 150 μm)). Performing the particle size control allows the particles to each have a controlled size before surface crosslinking.

Further, in the present invention, (i) the particle size before surface crosslinking (that is, the particle size of the water absorbent resin powder to be subjected to the surface crosslinking step) and (ii) the particle size of the particulate water absorbing agent of the present invention are preferably such that particles having passed through a 150-μm mesh as defined through a standard-sieve classification are in an amount of 5 mass % or less, 3 mass % or less, or 2 mass % or less.

In other words, in the present invention, (i) the water absorbent resin powder before surface crosslinking (that is, the water absorbent resin powder to be subjected to the surface crosslinking step) and (ii) the particulate water absorbing agent of the present invention are each arranged such that particles having passed through a 150-μm mesh as defined through a standard-sieve classification are contained in an amount of preferably 5 mass % or less, more preferably 3 mass % or less, particularly preferably 2 mass % or less.

The expression "particles having passed through a 150-μm mesh as defined through a standard-sieve classification" refers to fine powder having passed through a JIS standard sieve having a mesh size of 150 μm.

Further, particles that do not pass through a 600-μm mesh, that is, particles with sizes of 600 μm or larger, account for 20 mass % or less, more preferably 15 mass % or less, still more preferably 12 mass % or less, particularly preferably 10 mass % or less, of the entire water absorbent resin powder (Although the lower limit is 0 mass %, it may be approximately 1 mass % in view of, for example, productivity and yield after the classification).

In other words, the water absorbent resin powder before surface crosslinking and the particulate water absorbing agent of the present invention each contain particles with sizes of 600 μm or larger (particles incapable of passing through a JIS standard sieve having a mesh size of 600 μm) in an amount of 20 mass % or less, more preferably 15 mass % or less, still more preferably 12 mass % or less, particularly preferably 10 mass % or less (Although the lower limit is 0 mass %, it may be approximately 1 mass % in view of, for example, productivity and yield after the classification).

If the water absorbent resin powder before surface crosslinking or the particulate water absorbing agent of the present invention contains particles with sizes of 600 μm or larger (that is, particles incapable of passing through a JIS standard sieve having a mesh size of 600 μm) in an amount of more than 20 mass % relative to the entire water absorbent resin before surface crosslinking or particulate water absorbing agent, such a large amount may (i) prevent sufficient expression of liquid transportability (capillary force) between gel particles when the water absorbent resin powder before surface crosslinking or particulate water absorbing agent of the present invention is swollen and thus (ii) decrease the speed of absorbing liquid, with the result of a decrease in the re-wet.

More preferably, (i) the particle size before surface crosslinking (that is, the particle size of the water absorbent resin powder to be subjected to the surface crosslinking step) and (ii) the particle size of the particulate water absorbing agent of the present invention are each such that particles that do not pass through a 710-μm mesh are in an amount of 5 mass % or less, 3 mass % or less, or 1 mass % or less (the lower limit being 0 mass %).

In other words, (i) the water absorbent resin powder before surface crosslinking (water absorbent resin powder to be subjected to the surface crosslinking step) and (ii) the particulate water absorbing agent of the present invention are each arranged such that particles that do not pass through a 710-μm mesh as defined through a standard-sieve classification are contained in an amount of preferably 5 mass % or less, more preferably 3 mass % or less, particularly preferably 1 mass % or less (Although the lower limit is 0 mass %, it may be approximately 0.1 mass %).

A more preferable particle size distribution before surface crosslinking is a particle size distribution in which particles that pass through a sieve having a mesh size of 600 μm and that do not pass through a sieve having a mesh size of 150 μm (this may be referred to as "600 to 150 μm") are contained in an amount of 80 mass % or more. Particles that pass through a sieve having a mesh size of 300 μm are contained in an amount of preferably 10 mass % or more, more preferably 15 mass % or more, particularly preferably 20 mass % or more. The content of such particles has an upper limit of preferably 60 mass % or lower, more preferably 50 mass % or lower, still more preferably 40 mass % or lower, particularly preferably 30 mass % or lower.

The expression "particles that do not pass through a 710-μm mesh as defined through a standard-sieve classification" refers to the content of particles incapable of passing through a JIS standard sieve having a mesh size of 710 μm.

Outside the above particle size range (that is, the particle size range in which the water absorbent resin powder to be subjected to the surface crosslinking step has a particle size such that particles that do not pass through a 710-μm mesh as defined through a standard-sieve classification are contained in an amount of 5 mass % or less), it is difficult to produce the particulate water absorbing agent of the present invention. In view of that, the production method of the present invention preferably includes a first classification step before surface crosslinking and more preferably further includes a second classification step after surface crosslinking.

The first classification step is a classification step performed before surface crosslinking, whereas the second classification step is a classification step performed after surface crosslinking. Specifically, the first classification step and the second classification step differ from each other merely in timing of classification, and may thus be identical to each other in operation details. For instance, the first classification step and the second classification step may both use the above JIS standard sieves and classification device for classification.

The first classification step and the second classification step may use a sieve with the same mesh size. The first classification step and the second classification step may alternatively use sieves with different mesh sizes as appropriate in correspondence with a change in the particle size of the water absorbent resin during the surface crosslinking step and/or its subsequent granulating step. For instance, the second classification step may simply separate only fine powder, separate only agglomerates, or use a sieve having a different mesh size.

(Conventional Particle Size Control)

There have been known many water absorbent resins each containing, as a main component, particles with sizes of 850 to 150 μm or 850 to 106 μm (that is, water absorbent resins each containing, as a main component, particles with sizes of 850 μm to 150 μm or 850 to 106 μm as defined through a standard-sieve classification) as in the above Patent Literatures (see, for example, Patent Literature 5, or U.S. Pat. No. 6,605,673). The present invention, in contrast, has an upper limit of 600 μm as the inventors of the present invention has discovered that setting the upper limit of the particle size to 600 μm is important to the SST and FST described below of the present invention.

There have also been known, in relation to the particle size of water absorbent resin powder, a technique in which the main component is particles with sizes of 600 to 150 μm (see Patent Literatures 17 to 19) and a technique in which the main component is particles with sizes of 297 to 149 μm (see Patent Literature 20). None of Patent Literatures 17 to 20, however, suggests (i) the SST or FST described below of the present invention or (ii) a method for producing the water absorbing agent of the present invention (that is, a method of the present invention for controlling the SST or FST).

Specifically, the inventors performed a particular control of polymerization and water absorption capacity and set the conditions so that 80 mass % or more of the particulate water absorbing agent of the present invention is within a range of 150 μm to 600 μm as defined through a standard-sieve classification. The inventors have thus discovered that such setting is important to the SST and FST described below of the present invention.

(Another Particle Size for the Present Invention)

The water absorbent resin powder of the present invention before surface crosslinking and the particulate water absorbing agent produced therefrom may each have any mass average particle diameter (D50). The mass average particle diameter is, however, preferably 200 to 500 µm, more preferably 250 to 450 µm or less, still more preferably 300 to 430 µm. A mass average particle diameter of smaller than 200 µm may lead not only to poor usability, but also to a large amount of dust, with the result of a poor liquid transportation property.

The term "mass average particle diameter (D50)" as used in the present specification refers to a value obtained by, for example, (i) classifying 10.0 g of a particulate water absorbing agent in a Ro-tap (product name) classification device with use of JIS standard sieves (JIS Z8801-1 (2000)) having respective mesh sizes of 850 µm, 710 µm, 600 µm, 500 µm, 425 µm, 300 µm, 212 µm, 150 µm, 106 µm, and 75 µm for sufficient equilibrium (normally for 10 minutes) and (ii) plotting a residual percentage R for each particle size on a logarithmic probability paper to read a particle size corresponding to R=50 mass %.

The above description of the mass average particle diameter directly applies not only to a water absorbent resin before surface crosslinking but also to a particulate water absorbing agent as a final product discussed under (C) below.

The water absorbent resin and water absorbing agent produced as above may each be in the form of a sheet, a fiber, a film, or a gel in correspondence with the intended use. However, since the water absorbing agent is in the form of particles (powder), the water absorbent resin for use is preferably also in the form of a powder. In the case where the water absorbent resin and water absorbing agent are in the form of a powder, the water absorbent resin has a larger surface area per unit weight, with the result of an increased water absorbing speed. In the case where water absorbent resin and water absorbing agent are in the form of a powder, the shape of the particles is not limited to any particular one, and may be, for example, a sphere, a pulverized shape, an irregular shape, or a granulated product thereof (that is, a product formed of a plurality of particles bound together). However, in view of the size of the surface area, it is preferable to use (i) particles in an irregularly pulverized shape that are produced through the pulverization step (that is, the shape of a crushed product of the dried polymer) or a granulated product thereof.

If the water absorbent resin or water absorbing agent has a bulk specific gravity (defined by JIS K-3362) outside an appropriate bulk specific gravity range, it may lead to a decreased property in a process on an industrial scale. In view of that, the bulk specific gravity is within a range of preferably 0.40 to 0.80 g/ml, more preferably 0.50 to 0.75 g/ml, still more preferably 0.60 to 0.73 g/ml. A bulk specific gravity of less than 0.40 g/ml or more than 0.90 g/ml may let the water absorbent resin and water absorbing agent be easily damaged during the production process, with the result of decreased physical properties.

(3-2) Another Method Optionally Including a Pulverization Step and a Classification Step (Reverse Phase Suspension Polymerization, Spray Drop Polymerization)

The particle size is important in the production method of the present invention as described under (3) above. Aqueous solution polymerization, for example, requires a pulverization step and possibly a classification step. It is, however, merely necessary that the particle size be as described under (3) above after polymerization and drying. Thus, to control the particle diameter within the above range simultaneously with the polymerization, another method (3-2) optionally including a pulverization step and a classification step may be used such as (i) reverse phase suspension polymerization for the monomer of (1) above in a hydrophobic solvent and (ii) spray drop polymerization in a gas phase. The particles may be further granulated for a predetermined particle size during the polymerization step or drying step of reverse phase suspension polymerization or spray drop polymerization. Performing reverse phase suspension polymerization or spray drop polymerization allows production of water absorbent resin particles each in the shape of a sphere or of an agglomerate of spheres.

Reverse phase suspension is suitably performed by a granulation method involving a two-stage polymerization. Reverse phase suspension polymerization is followed by, for example, drying that involves azeotropic dehydration in a hydrophobic organic solvent, whereas spray drop polymerization in a gas phase is followed by, for example, drying with a fluidized bed. The method (3-2) optionally involving a pulverization step and a classification step can include (i) reverse phase suspension polymerization described in, for example, not only five U.S. patents cited under (1) above on reverse phase suspension polymerization, but also WO2012/053121, WO2012/014750, WO2012/014749, and WO2012/014747 or (ii) spray drop polymerization described in, for example, WO2011/026876A1 and WO2010/003855. These techniques can be referred to as appropriate to perform polymerization and drying, and optionally the agglomerates are crushed and classified as necessary, to control the particle size.

In the present invention, the pulverization and optional classification described under (3) above may be performed to control the particle size within the range of (3), or alternatively reverse phase suspension polymerization or spray drop polymerization described under (3-2) may be performed to control the particle size within the range of (3). For more effective attainment of the object of the present invention, the particle size is controlled through the pulverization and optional classification described under (3) rather than the method of (3-2).

(4) Surface Crosslinking Step

The method of the present invention for producing a water absorbing agent includes a drying step of producing a classified product through the pulverization and classification step performed on the dried product produced through the drying step described under (2) above. The method of the present invention for producing a particulate water absorbing agent, in other words, includes the above-described pulverization step (or pulverization step and classification step) after the drying step described under (2) above.

A surface crosslinking step is performed with use of a surface-crosslinking agent containing a hydroxyl group and/or a derivative group thereof until the swelling rate (CRC) is within a range of 32 to 50 g/g and the swelling rate (CRC) is decreased by 3 to 15 g/g (that is, the surface-crosslinking agent is used so that the swelling rate (CRC) is decreased by 3 to 15 g/g to fall within a range of 32 g/g to 50 g/g for production of a surface-crosslinked water absorbent resin powder). More preferably, the surface crosslinking is performed with use of a plurality of organic surface-crosslinking agents. The production method is, however, not limited to any particular one as long as it is possible to produce the particulate water absorbing agent of the present invention. (The decrease in the swelling rate (CRC) is not corrected on the basis of the moisture content. The decrease in the swelling rate (CRC) is defined by the water absorption capacity CRC of a water absorbent resin optionally containing water.)

The water absorbent resin for use in the water absorbing agent of the present embodiment simply needs to be produced through the crosslinking polymerization and drying of (1) to (3) (or (3-2)) above. The water absorbent resin is, however, preferably further surface-crosslinked (secondary crosslinking). In other words, although the water absorbent resin powder for use in the production of the particulate water absorbing agent of the present invention simply needs to be produced through crosslinking polymerization and drying during the steps (1) to (3) (or (3-2)) above, the water absorbent resin powder is preferably further surface-crosslinked (secondary crosslinking).

Surface-crosslinking the water absorbent resin powder (secondary crosslinking) can improve the swelling rate under load (AAP) and liquid permeability (for example, SFC/GBP), allows a swollen particulate water absorbing agent to retain gaps between particles, and improves the water-absorbing performance of a diaper including the water absorbent resin powder.

(Surface-Crosslinking Agent)

The surface crosslinking can be performed with use of any of various crosslinking agents. Typical examples, from a viewpoint of physical properties, include (i) organic surface-crosslinking agents such as a polyhydric alcohol compound, an epoxy compound, a polyhydric amine compound or condensate thereof with a haloepoxy compound, an oxazoline compound, a mono, di, or polyoxazolidinone compound, and an alkylenecarbonate compound and (ii) inorganic surface-crosslinking agents such as polyhydric metal salt.

The surface-crosslinking agent for use in the present embodiment is an organic or inorganic surface-crosslinking agent, in particular an organic surface-crosslinking agent. Specifically, such a surface-crosslinking agent is disclosed in, for example, U.S. Pat. Nos. 5,409,771, 6,228,930, 6,071,976, and 6,254,990 as examples. Examples of the surface-crosslinking agent include, but are not limited to, (i) polyhydric alcohol compounds such as mono, di, tri, tetra, or polyethyleneglycol, monopropyleneglycol, 1,3-propane diol, dipropyleneglycol, 2,3,4-trimethyl-1,3-pentanediol, polypropylene glycol, glycerin, polyglycerin, 2-butene-1,4-diol, 1,4-butandiol, 1,3-butandiol, 1,5-pentanediol, 1,6-hexanediol, and 1,2-cyclohexanedimethanol, (ii) epoxy compounds (in particular, polyvalent glycidyl compounds) such as ethyleneglycol diglycidyl ether and glycidol, (iii) polyhydric amine compounds such as ethylenediamine, diethylenetriamine, triethylenetetramine, tetraethylenepentamine, pentaethylenehexamine, polyethylene imine, and polyamidepolyamine, (iv) haloepoxy compounds such as epichlorohydrin, epibromhydrin, and α-methyl epichlorohydrin, (v) oxazolidinone compounds such as a condensate of the polyhydric amine compound and the haloepoxy compound and 2-oxazolidinone, (vi) alkylenecarbonate compounds such as ethylene carbonate (see U.S. Pat. No. 5,409,771), and the like.

The surface-crosslinking agent is, to maximize the effects of the present embodiment, at least an organic or inorganic surface-crosslinking agent, in particular an organic surface-crosslinking agent, among the above surface-crosslinking agents. The surface-crosslinking agent is, for example, a surface-crosslinking agent containing a hydroxyl group and/or a derivative group thereof, in particular a surface-crosslinking agent selected from a polyhydric alcohol, an amino alcohol, and a derivative thereof (in particular, a carbonic acid esters and an amides). More specifically, the surface-crosslinking agent is preferably one or two kinds of an oxazolidinone compound, an alkylenecarbonate compound, and a polyhydric alcohol compound. The surface-crosslinking agent is particularly preferably a polyhydric alcohol having 2 to 10 carbon atoms, preferably 3 to 8 carbon atoms. An alkylenecarbonate compound has a cyclic carbonic acid ester structure of a polyhydric alcohol, and an oxazolidinone compound has a cyclic carbonic acid ester structure of an alkanolamine. Ethylene carbonate (or 1,3-dioxolane-2-on), for example, is a derivative of the polyhydric alcohol for the present invention as it is made of ethylene glycol and ethylene oxide.

The production of the particulate water absorbing agent of the present invention preferably involves surface crosslinking with use of a plurality of organic surface-crosslinking agents (in other words, the production preferably involves use of two or more kinds of organic compounds as the surface-crosslinking agent), at least one kind of which is a surface-crosslinking agent containing a hydroxyl group and/or a derivative group thereof. The use of a plurality of organic surface-crosslinking agents presumably allows such different surface-crosslinking agents to impart permeability and reactivity to the water absorbent resin and form the most suitable cross-linked layer to provide the particulate water absorbing agent of the present invention.

The plurality of organic surface-crosslinking agents, specifically the plurality of organic surface-crosslinking agents different from each other in reactivity and permeability, are preferably such a combination of surface-crosslinking agents as (i) a plurality of polyhydric alcohols, (ii) a combination of a polyhydric alcohol and an oxazolidinone compound, (iii) a combination of a polyhydric alcohol and an alkylenecarbonate compound, (iv) a combination of a polyhydric alcohol and a polyvalent glycidyl compound, (v) a combination of an alkylenecarbonate compound and a polyvalent glycidyl compound, and (vi) a combination of a polyhydric alcohol, a polyvalent glycidyl compound, an alkylenecarbonate compound, and a polyvalent glycidyl compound. In particular, at least one kind of the plurality of surface-crosslinking agents is a polyhydric alcohol, particularly preferably one or two kinds of polyhydric alcohols each having 2 to 10 carbon atoms, preferably 3 to 8 carbon atoms. The alkylenecarbonate compound includes one or two kinds of compounds selected from ethylene carbonate (or 1,3-dioxolane-2-on) and propylene carbonate.

The surface-crosslinking agent is used in an amount (in the case where a plurality of surface-crosslinking agents are used, the total amount) that depends on, for example, the compounds to be used and a combination thereof. The amount is, however, preferably within a range of 0.001 part by mass to 10 parts by mass, more preferably within a range of 0.01 part by mass to 5 parts by mass, relative to 100 parts by mass of the water absorbent resin. This "water absorbent resin" refers to the water absorbent resin powder produced through the pulverization step (or pulverization step and classification step).

Further, in the case where a plurality of surface-crosslinking agents are used in combination with each other, the total amount and the respective amounts of the plurality of surface-crosslinking agents are each within the above range. In the case where a surface-crosslinking agent containing a hydroxyl group and/or a derivative group thereof is used together with another surface-crosslinking agent (for example, a polyvalent glycidyl compound), those surface-crosslinking agents are used at a weight ratio of 5/5 to 100/1 or 7/3 to 20/1. The weight ratio is, however, not limited to any particular one as long as it is possible to produce the particulate water absorbing agent of the present invention.

(Crosslinking Reaction Condition)

The present embodiment preferably uses water as a solvent for the surface-crosslinking agent. Such water is used in an amount that depends on the moisture content of the water absorbent resin to be used (that is, the water absorbent resin powder). The amount is, however, typically within a range of 0.5 to 20 parts by mass, preferably 0.5 to 10 parts by mass, relative to 100 parts by mass of the water absorbent resin.

The present embodiment may use a hydrophilic organic solvent except for water. Such a hydrophilic organic solvent is used in an amount that is within a range of 0 to 10 parts by mass, preferably 0 to 5 parts by mass, more preferably 0 to 3 parts by mass, relative to the water absorbent resin. Further, a surfactant, an inorganic salt or organic salt, and/or an organic acid or inorganic acid may be added to the surface-crosslinking agent aqueous solution during or not during its mixing (in other words, the present embodiment may use, in combination with the surface-crosslinking agent aqueous solution, one or more kinds selected from a surfactant, an inorganic salt, an organic salt, an organic acid, and an inorganic acid) for an improved mixing property and reactivity. In addition, the present embodiment may further use, for example, a reducing agent, a chelating agent, an anti-coloring agent, and/or a deodorant agent in combination with the surface-crosslinking agent aqueous solution to add a function.

The present embodiment may use any of various mixing methods, but preferably uses a method of (i) mixing water and/or a hydrophilic organic solvent in advance with the surface-crosslinking agent as necessary and then (ii) spraying or dropping, more preferably spraying, the surface-crosslinking agent aqueous solution onto the water absorbent resin. The surface-crosslinking agent aqueous solution is sprayed in the form of liquid droplets with sizes of preferably 300 µm or less, more preferably 200 µm or less (the lower limit being preferably 1 µm or larger).

The surface-crosslinking agent or its solution is added to the water absorbent resin during the step of (3) or (3-2) above. The surface-crosslinking agent or its solution may be added to the water absorbent resin powder directly or to the water absorbent resin powder dispersed in an organic solvent such as heptane. The surface-crosslinking agent or its solution is preferably sprayed onto the water absorbent resin powder directly. Suitable mixers include various rotary mixers such as Shgugi mixer, Turbulizer, Lodige mixer, and Lindor mixer.

The water absorbent resin is, after being mixed with the surface-crosslinking agent, preferably heat-treated. During this heat treatment, the water absorbent resin mixed with the surface-crosslinking agent, that is, the mixture of the water absorbent resin and the surface-crosslinking agent, is heated to a temperature within a range of preferably 100 to 250° C., more preferably 150 to 250° C. The mixture is heated over a period within a range of preferably 1 minute to 2 hours. As suitable examples of a combination of the temperature and period, the mixture is heated at 180° C. for 0.1 to 1.5 hours or at 200° C. for 0.1 to 1 hour. The present embodiment may, as necessary, perform a cooling step a certain time period after the heat treatment to end the crosslinking reaction.

(Crosslinking Density)

The above surface crosslinking is performed with adjustment of the amount of the surface-crosslinking agent and/or reaction temperature and time so that the swelling rate (CRC (ERT 442.2-01)) will preferably be decreased by 1 to 20 g/g, more preferably 3 to 15 g/g, over the water absorbent resin before surface crosslinking (that is, the water absorbent resin powder produced through the pulverization step (or pulverization step and classification step)). The surface crosslinking can increase the swelling rate under load (AAP (ERT 442.2-02)) after surface crosslinking to 20 to 45 g/g, more preferably 24 to 40 g/g.

(Particle Size Control/Preferably Second Classification Step)

As described above, the water absorbent resin produced through the particle size control step (3) (that is, the pulverization step (or pulverization step and classification step)) and the surface crosslinking step (4) has particles with sizes adjusted as necessary to particular values through (i) a particle size control before surface crosslinking and (ii) a particle size control after surface crosslinking. The water absorbent resin preferably contains (i) particles with sizes of smaller than 850 µm and not smaller than 150 µm as defined through a standard-sieve classification in an amount of 90 mass % or more and 100 mass % or less, relative to the entire water absorbent resin and (ii) particles with sizes of 600 µm or larger as defined through a standard-sieve classification in an amount of 0 mass % or more and 20 mass % or less, relative to the entire water absorbent resin. The amount of particles with sizes of smaller than 850 µm and not smaller than 150 µm is more preferably 95 mass % or more, still more preferably 98 mass % or more, relative to the entire water absorbent resin. The amount of particles with sizes of 600 µm or larger is more preferably 15 mass % or less, still more preferably 12 mass % or less, particularly preferably 10 mass % or less, with the lower limit being 0 mass %.

The water absorbent resin has a mass average particle diameter (D50) of preferably 200 to 550 µm, more preferably 250 to 500 µm. The water absorbent resin and the particulate water absorbing agent each have particles with diameters that are preferably controlled through the pulverization and classification of (3) above before surface crosslinking. The particle diameters may be further adjusted as necessary through pulverization of agglomerates (that is, an operation of grinding particle agglomerates), or such steps as classification or granulation, after surface crosslinking. The surface crosslinking step (4) is preferably followed by a second classification step at any stage.

(5) Additive Mixing Step of Mixing Water-Insoluble Inorganic Fine Particles and/or Water-Soluble Polyhydric Metal Cations The method of the present invention for producing a water absorbing agent further includes an additive mixing step (liquid permeability improving agent adding step) (5) of mixing water-insoluble inorganic fine particles (and as necessary water-soluble polyhydric metal cations) which additive mixing step is performed simultaneously with or after the surface crosslinking step described under (4) above.

Further, the particulate water absorbing agent of the present invention can contain any of various additives to prevent gel blocking. The particulate water absorbing agent can contain, for example, water-insoluble inorganic fine particles and/or water-soluble polyvalent metal ions, preferably water-insoluble inorganic fine particles, more preferably water-insoluble inorganic fine particles and water-soluble polyvalent metal ions in combination with each other.

(Mixing Method)

The water-insoluble inorganic fine particles and water-soluble polyhydric metal cations may be mixed as powder (that is, mixed while both in a powder state). The mixing may alternatively involve use of a solvent (preferably, water)

to mix a dispersion (preferably, an aqueous dispersion) of the water-insoluble inorganic fine particles with a solution (preferably, an aqueous solution) of the water-soluble polyhydric metal cations. In the case where a solvent (preferably, water) for the mixing is used, the solvent may be dried and/or (to accelerate the mixing) heated as necessary.

Examples of the method of adding water-insoluble inorganic fine particles and/or water-soluble polyhydric metal cations during the surface crosslinking step (4) include, but are not limited to:

(i) a method of mixing, with the water absorbent resin, a surface-crosslinking agent aqueous solution containing water-insoluble inorganic fine particles and/or water-soluble polyhydric metal cations;

(ii) a method of mixing in advance water-insoluble inorganic fine particles and/or water-soluble polyhydric metal cations with the water absorbent resin (that is, the water absorbent resin powder produced through the pulverization step (or pulverization step and classification step)) and mixing the surface-crosslinking agent aqueous solution with the water absorbent resin;

(iii) a method of mixing in advance water-insoluble inorganic fine particles and/or water-soluble polyhydric metal cations with the water absorbent resin while separately mixing a surface-crosslinking agent aqueous solution with the water absorbent resin;

(iv) a method of mixing water-insoluble inorganic fine particles and/or water-soluble polyhydric metal cations with the water absorbent resin in a heat treatment device to be used for surface crosslinking (and/or a cooling device for optional use).

For the addition of water-insoluble inorganic fine particles and/or water-soluble polyhydric metal cations after the end of the surface crosslinking step (4) (that is, for performing the liquid permeability improving agent adding step as a downstream step of the surface crosslinking step), the surface-crosslinked water absorbent resin powder (water absorbent resin powder that is surface-crosslinked) simply needs to be mixed, during any and/or additional step after the end of the surface crosslinking step, with (i) water-insoluble inorganic fine particles and/or water-soluble polyhydric metal cations, (ii) a solution containing water-insoluble inorganic fine particles and/or water-soluble polyhydric metal cations, and/or (iii) a dispersion containing water-insoluble inorganic fine particles and/or water-soluble polyhydric metal cations.

For instance, water-insoluble inorganic fine particles and water-soluble polyhydric metal cations may be added, during the transporting step or second classification step after surface crosslinking, to fluid water absorbent resin powder to be mixed therewith. It is also possible to optionally use a separate mixer and/or solvent dryer.

In the case where water is used for the mixing, such water is used in an amount of 0.1 to 10 parts by mass, more preferably approximately 0.5 to 5 parts by mass, relative to 100 parts by mass of the water absorbent resin.

(Water-Insoluble Inorganic Fine Particles)

The water-insoluble inorganic fine particles are, for example, of a material selected from the group consisting of silicon dioxide, silica, silicate, titanium dioxide, aluminum oxide, magnesium oxide, zinc oxide, talc, calcium phosphate, clay, diatomaceous earth, zeolite, bentonite, kaolin, hydrotalcite, and activated clay. A suitable material is preferably silicon dioxide and/or aluminum oxide, more preferably silicon dioxide (amorphous silica).

The water-insoluble inorganic fine particles are contained in an amount of preferably 0.05 part by mass or more and 5.0 parts by mass or less, more preferably 0.2 part by mass or more and 1.0 part by mass or less, still more preferably 0.3 part by mass or more and 0.7 part by mass or less, particularly preferably 0.3 part by mass or more and 0.5 part by mass or less, relative to 100 parts by mass of the particulate water absorbing agent of the present invention.

The water-insoluble inorganic fine particles are added in an amount of preferably 0.05 part by mass or more and 5.0 parts by mass or less, more preferably 0.2 part by mass or more and 1.0 part by mass or less, still more preferably 0.3 part by mass or more and 0.7 part by mass or less, most preferably 0.3 part by mass or more and 0.5 part by mass or less, relative to 100 parts by mass of the water absorbent resin powder and/or surface-crosslinked water absorbent resin powder. This arrangement allows the water-insoluble inorganic fine particles to be contained in the particulate water absorbing agent in an amount within the above preferable range.

Adding the water-insoluble inorganic fine particles in an amount of less than 0.05 part by mass will fail to allow a sufficient gel-blocking preventing effect to be produced. Adding the water-insoluble inorganic fine particles in an amount of more than 5.0 parts by mass is economically disadvantageous, and may additionally lead to a decrease in the swelling property of the water absorbent resin. The water-insoluble inorganic fine particles are preferably so water-insoluble that it is dissolved in 100 g of water (at 25° C.) in an amount of 100 mg or less, 10 mg or less, or 1 mg or less. The water-insoluble inorganic fine particles each have a particle size (volume average particle size measured with use of a laser) of preferably 50 μm or less, more preferably 10 μm or less, still more preferably 5 μm or less, particularly preferably 1 μm or less. The particle size has a lower limit of preferably 1 nm or higher, more preferably 5 nm or higher.

(Polyvalent Metal Ions)

The water-soluble polyvalent metal ions are typically added in the form of polyhydric metal salt. The water-soluble polyvalent metal ions are more preferably a compound containing water-soluble polyhydric metal cations which compound contains, as the metal ions, metal cations having a valence of 3 or more such as aluminum, zirconium, chrome, titanium, and zinc. Preferable examples of the metal cations having a valence of 3 or more include aluminum, zirconium, and titanium, among which aluminum is the most preferable.

Examples of the aluminum include (i) organic salts such as aluminum acetate and aluminum lactate and/or (ii) hydroxides such as aluminium hydroxide. The aluminum may be, for example, aluminum sulfate tetradecahydrate to octadecahydrate (or anhydride), aluminum potassium sulfate dodecahydrate, aluminum sodium sulfate dodecahydrate, aluminum chloride, or polyaluminum chloride. The aluminum is suitably and preferably aluminum sulfate and/or a hydrate thereof (for example, tetradecahydrate to octadecahydrate).

The water-soluble polyvalent metal ions are contained in an amount (as defined in terms of the mass of the water-soluble polyhydric metal cations; excluding the mass of counter anions) of preferably 0.01 part by mass or more and 5.0 parts by mass or less, more preferably 0.05 part by mass or more and 0.7 part by mass or less, still more preferably 0.1 part by mass or more and 0.5 part by mass or less, relative to 100 parts by mass of the particulate water absorbing agent of the present invention.

The water-soluble polyvalent metal ions are added in an amount of preferably 0.01 part by mass or more and 5.0 parts by mass or less, more preferably 0.1 part by mass or more and 1.0 part by mass or less, still more preferably 0.2 part by mass or more and 0.7 part by mass or less, particularly preferably 0.3 part by mass or more and 0.5 part by mass or less, relative to 100 parts by mass of the water absorbent resin powder and/or surface-crosslinked water absorbent resin powder. This arrangement allows the water-soluble polyvalent metal ions to be contained in the particulate water absorbing agent in an amount within the above preferable range.

In the case where the polyhydric metal cations are used in the form of a powder, the particle size (volume average particle size measured with use of a laser) is preferably 200 μm or less, more preferably 100 μm or less, still more preferably 50 μm or less, particularly preferably 10 μm or less. The polyhydric metal cations are preferably added in the form of an aqueous solution and immobilized on the particle surface (the lower limit of the particle size being preferably 0.01 μm, more preferably approximately 0.1 μm).

(6) Other Additives and Steps

The method of producing the particulate water absorbing agent of the present invention may further include, as necessary, a step of imparting any of various functions to the water absorbent resin which step is performed simultaneously with or separately from the steps (1) to (5). The step is, for example, of adding (i) a hydrophilic polymer such as a deodorant agent, an antibacterial agent, a perfume, a foaming agent, a pigment, a dye, hydrophilic short fiber, a plasticizing agent, an adhesive, metal soap, a surfactant, a fertilizer, an oxidizing agent, a reducing agent, water, a salt, a chelating agent, a disinfectant, and polyethyleneglycol, (ii) a hydrophobic polymer such as paraffin, (iii) a thermoplastic resin such as polyethylene and polypropylene, (iv) a thermosetting resin such as polyester resin and urea resin, or the like. These additives are each used in an amount of 0 to 10 parts by mass, preferably 0 to 1 part by mass, relative to 100 parts by mass of the water absorbent resin at the time of adding such additives.

The above various additives to be added for the present invention are mixed through any method. Examples of the method include a method of mixing an additive in the form of an aqueous solution, a method of mixing an additive in the form of a slurry, a method of mixing an additive in the form of a powder, and the like. Further examples include methods described in Japanese Translation of PCT International Application, Tokuhyo, No. 2002-539281, Japanese Translation of PCT International Application, Tokuhyo, No. 2002-538275 (method of adding an additive in the form of an aqueous solution before a surface treatment), Japanese Translation of PCT International Application, Tokuhyo, No. 2001-523289 (method of dry-blending an additive with a particulate water absorbing agent and then adding a binding agent to the mixture), Japanese Translation of PCT International Application, Tokuhyo, No. 2001-523287 (method of adding an additive in the form of an aqueous solution after a surface treatment) and the like.

(C) Particulate Water Absorbing Agent of the Present Invention

The present invention provides, through the production method described under (B) above as an example, a novel water absorbing agent, specifically a particulate water absorbing agent containing a polyacrylic acid (salt)-based water absorbent resin as a main component, the water absorbing agent having a swelling rate (CRC) of 32 to 45 g/g relative to 0.9-mass % saline, the water absorbing agent including, at a proportion of 80 mass % or more, a particle having a size of 600 to 150 μm as defined through a standard-sieve classification, the water absorbing agent having a second-instance pure-water 50-fold swelling time (SST (in seconds)) of 70 seconds or less, the second-instance pure-water 50-fold swelling time (SST (in seconds)) being not longer than the first-instance pure-water 50-fold swelling time (FST (in seconds)) by 10 seconds or longer, or SST−FST≤10.

The particulate water absorbing agent of the present invention has an excellent gel property. The particulate water absorbing agent can exhibit such an excellent gel property because it not only has a certain swelling rate (CRC) or higher and a certain particle size distribution or higher, but also has a new parameter that had not been considered at all and that is attained with the following characteristics: a second swelling time (SST) being 70 seconds or less; and the difference between a swelling time (FST) involving use of pure water and the second swelling time (SST) being 10 seconds or less. There have been proposed and publicly known various gel-blocking preventing techniques such as surface reforming techniques (see Patent Literatures 2 to 5), addition of an inorganic compound (see Patent Literatures 6 to 9), and a technique of combinational use of a chain transfer agent for improvement of gel strength (see Patent Literature 10). These techniques are, however, problematic in that they may (i) fail to produce sufficient improvement or (ii) require an extremely large amount of an additive or the like for a sufficient effect.

The inventors of the present invention have conducted diligent studies to produce a particulate water absorbing agent having an excellent gel property, and have discovered as a result that a particulate water absorbing agent has an excellent gel property only in the case where it not only has a certain swelling rate (CRC) or higher and a certain particle size distribution or higher, but also has the characteristics of (i) a second swelling time (SST) being 70 seconds or less and (ii) the difference between a swelling time (FST) involving use of pure water and the second swelling time (SST) being 10 seconds or less. Although the mechanism has not been fully understood yet, performing polymerization under particular conditions allows production of a high-strength gel capable of retaining more gaps in the gel even after the gel has been swollen once. In other words, the present invention can prevent a decrease in liquid transportability which decrease arises from gel blocking, and allows the particulate water absorbing agent to have a surface area for liquid absorption at a sufficient rate even after the gel has been swollen once, that is, even at the second instance and later. The inventors of the present invention have discovered an index of the degree of liquid absorption at the second instance and later and also discovered that a particulate water absorbing agent has an excellent gel property in the case where it satisfies a certain swelling rate (CRC) or higher. The inventors have thus finally completed the present invention.

(Swelling Rate (CRC)) (ERT 441.2-02)

The particulate water absorbing agent of the present invention has a swelling rate (CRC) of 32 to 50 g/g, preferably 32 to 45 g/g, more preferably 32 to 43 g/g, still more preferably 32 to 40 g/g, particularly preferably 33 to 38 g/g, most preferably 34 to 38 g/g, relative to 0.9-mass % saline. A CRC of lower than 32 g/g will lead to a smaller total absorption amount in the case where the particulate water absorbing agent is used in an absorbent body. This may require an increase in the amount of use of the particulate water absorbing agent, and may be disadvantageous in cost. Further, since a higher upper limit for the CRC typically leads to a decrease in properties such as a swelling rate under load (AAP) described below, the upper limit is approximately 50 g/g.

(Swelling Rate Under Load (AAP)) (ERT 442.2-02)

The particulate water absorbing agent of the present invention has a swelling rate under load (AAP) of 24 g/g or higher, more preferably 26 g/g or higher, particularly preferably 28 g/g or higher, most preferably 30 g/g or higher, at 1.9 kPa relative to 0.9-mass % saline. An AAP of lower than 24 g/g may lead to an increase in, for example, the re-wet which increase arises from load in the case where the particulate water absorbing agent is used in an absorbent body (in particular, a disposable diaper). The upper limit of the AAP is preferably as high as possible, but is approximately 45 g/g or approximately 40 g/g for a balance with other physical properties.

(Degradable Soluble Component)

The water absorbing agent composition of the present invention contains a degradable soluble component in an amount of preferably 40 mass % or less, more preferably 30 mass % or less, still more preferably 25 mass % or less. The content of a degradable soluble component has a lower limit of preferably 5 mass % or more in view of other physical properties (in particular, water absorption capacity). A content of a degradable soluble component of more than 40 mass % is not preferable because the water absorbing agent composition may, in the case where it is used in an absorbent body and/or absorbent article described below (for example, a disposable diaper), lead to such problems as body fluids such as urine causing gel property deterioration, skin roughness, rash, and decrease in the property of removing bad odors.

The term "degradable soluble component" refers to a water-soluble content for which gel property deterioration due to urine is assumed. The degradable soluble component is measured with use of a physiological saline containing L-ascorbic acid, which facilitates gel property deterioration.

(DST)

The particulate water absorbing agent of the present invention is a particulate water absorbing agent having a DST of 10 seconds or less. The DST is preferably 7 seconds or less, more preferably 4 seconds or less, still more preferably 0 seconds or less, further still more preferably −3 seconds or less, particularly preferably −5 seconds or less, most preferably −7 seconds or less. A DST of more than 10 seconds indicates that it takes longer for the particulate water absorbing agent to be swollen at the second instance than at the first instance. In other words, the first swelling instance causes gel blocking and prevents the second and subsequent swelling instances. Specifically, while conventional water absorbing agents suffer from a large decrease in the second-instance pure-water 50-fold swelling time (SST (in seconds)), the water absorbing agent of the present invention is free from such a problem: The present invention also provides a water absorbing agent having a DST of 0 seconds or less, that is, having a second-instance pure-water 50-fold swelling time (SST (in seconds)) shorter than the first-instance pure-water 50-fold swelling time (FST (in seconds)). The lower limit value is preferably −30 seconds or more, more preferably −20 seconds or more, still more preferably −15 seconds or more, in view of other physical properties.

(SST)

The particulate water absorbing agent of the present invention has an SST of 70 seconds or less, more preferably 60 seconds or less, or particularly preferably 50 seconds or less, 45 seconds or less, or 40 seconds or less. In the case where the SST is more than 70 seconds, even if the difference between the SST and FST is small, their respective absolute values are both high (that is, the absolute value of the SST and the absolute value of the FST are both high). Using such a particulate water absorbing agent in an absorbent body may result in a low absorbing speed, failing to exhibit intended properties (Although the lower limit is preferably as high as possible, it is 1 second, more preferably approximately 5 seconds).

(Particle Size)

The particulate water absorbing agent of the present invention includes particles of which 80 mass % or more (the upper limit being 100 mass %) have sizes of 600 to 150 µm (as defined through a standard-sieve classification). The proportion is preferably controlled within the range described under (3) of (B) above (that is, preferably 85 mass % or more, more preferably 90 mass % or more, still more preferably 92 mass % or more).

The proportion of particles that pass through a 150-µm mesh is also preferably controlled within the range described under (3) of (B) above (that is, preferably 5 mass % or less, more preferably 3 mass % or less, still more preferably 2 mass % or less). The proportion of particles that do not pass through a 710-µm mesh is preferably controlled within the range described under (3) of (B) above (that is, preferably 5 mass % or less, more preferably 3 mass % or less, still more preferably 1 mass % or less).

A more preferable particle size distribution for the particulate water absorbing agent is a particle size distribution in which particles that pass through a sieve having a mesh size of 600 µm and that do not pass through a sieve having a mesh size of 150 µm (this may be referred to as "600 to 150 µm") are contained in an amount of 80 mass % or more. Particles that pass through a sieve having a mesh size of 300 µm are contained in an amount of preferably 10 mass % or more, more preferably 15 mass % or more, particularly preferably 20 mass % or more. The content of such particles has an upper limit of preferably 60 mass % or lower, more preferably 50 mass % or lower, still more preferably 40 mass % or lower, particularly preferably 30 mass % or lower.

The particulate water absorbing agent of the present invention may have any bulk specific gravity. The bulk specific gravity is, however, preferably controlled within the range described under (3) of (B) above. A bulk specific gravity of less than 0.40 g/ml or more than 0.90 g/ml may let the water absorbent resin and water absorbing agent be easily damaged during the production process, with the result of decreased physical properties.

The particulate water absorbing agent has a mass average particle diameter (D50) of preferably 200 to 500 µm, more preferably 250 to 450 µm or less, still more preferably 300 to 430 µm. A mass average particle diameter of smaller than 200 µm may lead not only to poor usability, but also to a large amount of dust, with the result of a poor liquid transportation property.

(Water-Insoluble Inorganic Fine Particles or Water-Soluble Polyhydric Metal Cations)

The particulate water absorbing agent preferably includes the water-insoluble inorganic fine particles described under (5) of (B) above, more preferably silicon dioxide. The water-insoluble inorganic fine particles are preferably contained in an amount of 0.05 part by mass or more and 5.0 parts by mass or less relative to 100 parts by mass of the particulate water absorbing agent of the present invention. The water-insoluble inorganic fine particles are contained in an amount of preferably 0.2 part by mass or more and 1.0 part by mass or less, more preferably 0.3 part by mass or more and 0.7 part by mass or less, still more preferably 0.3 part by mass or more and 0.5 part by mass or less, relative to 100 parts by mass of the particulate water absorbing agent.

The particulate water absorbing agent preferably further includes, in addition to the water-insoluble inorganic fine particles, the water-soluble polyhydric metal cations described under (5) of (B) above. The particulate water absorbing agent preferably includes water-soluble polyhydric metal salt in an amount of 0.01 part by mass or more and 5.0 parts by mass or less relative to 100 parts by mass of the particulate water absorbing agent of the present invention. The water-soluble polyhydric metal salt is contained in an amount of preferably 0.1 part by mass or more and 1.0 part by mass or less, more preferably 0.2 part by mass or more and 0.7 part by mass or less, still more preferably 0.3 part by mass or more and 0.5 part by mass or less, relative to 100 parts by mass of the particulate water absorbing agent.

The particulate water absorbing agent of the present invention may contain any amount of moisture (defined by measuring a drying loss caused by drying 1 g of the particulate water absorbing agent at 180° C. for 3 hours). The moisture content is, however, preferably 0.2 to 30 mass %, more preferably 0.3 to 15 mass %, particularly preferably 0.5 to 10 mass %. An excessively low moisture content (%) may lead to a decrease in the FST and/or a decrease in the stability of the water absorbing agent against impact (that is, a decrease in the physical properties which decrease arises from impact). On the other hand, an excessively high moisture content (%) may decrease the absolute amount of the water absorbent resin in the water absorbing agent, with the result of a decrease in the CRC and/or AAP or of a decrease in the fluidity that the water absorbent resin has in the case where it is in the form of particles.

(Other Components)

The particulate water absorbing agent of the present invention may contain any of the additives described under (6) of (B) above to have an additional or improved function. These additives are each used in an amount of 0 to 10 parts by mass, preferably 0 to 1 part by mass, relative to 100 parts by mass of the water absorbent resin at the time of adding such additives.

(D) Absorbent Body

The absorbent body of the present embodiment (referred to also as "water absorbent article" in the form of a finished product) is an absorbent body characteristically containing the particulate water absorbing agent of the present embodiment. The term "absorbent body" refers to a molded product of a material having a water-absorbing ability. The absorbent body preferably includes (i) the particulate water absorbing agent and a fiber material as water-absorbing materials and optionally (ii) a binder, a nonwoven fabric and/or the like to retain its shape. The absorbent body is optionally composited with, for example, a water-permeable back sheet to provide a water absorbent article (preferably a disposable diaper) as a finished product.

The absorbent body of the present embodiment is an absorbent body characteristically containing (i) a particulate water absorbing agent including, as a main component, a water absorbent resin that is produced by polymerizing a water-soluble unsaturated monomer and that has a cross-linked structure and optionally (ii) a hydrophilic fiber as another absorbent material.

The absorbent body of the present embodiment is preferably an absorbent body molded of a water absorbent resin and a hydrophilic fiber as main components. Such an absorbent body can be produced by molding the particulate water absorbing agent of the present embodiment and a hydrophilic fiber into a sheet tube etc.

In the present embodiment as well, the absorbent body may be, for example, (i) an absorbent body including fibers (for example, tissue paper) other than the hydrophilic fiber sandwiching a particulate water absorbing agent or (ii) an absorbent body prepared by simply hardening the particulate water absorbing agent with use of an adhesive or the like. Specifically, the absorbent body of the present embodiment may have a core concentration (that is, the content of the particulate water absorbing agent relative to the total mass of the particulate water absorbing agent and the hydrophilic fiber) of 100 mass %. However, in the case where the absorbent body further includes the hydrophilic fiber, the content of the particulate water absorbing agent relative to the total mass of the particulate water absorbing agent and the hydrophilic fiber (core concentration) is within a range of less than 100 mass %, preferably within a range of 10 to 90 mass %, more preferably within a range of 20 to 90 mass %, still more preferably within a range of 25 to 80 mass %, particularly preferably within a range of 40 to 80 mass %. A core concentration of less than 10 mass % is not preferable because using a small amount of the particulate water absorbing agent may not allow sufficient absorbing performance to be achieved. A core concentration of more than 90 mass % (in other words, the content of the hydrophilic fiber being less than 10 mass % relative to the total mass of the particulate water absorbing agent and the hydrophilic fiber) may not allow the effect of the use of the hydrophilic fiber to be produced sufficiently.

The particulate water absorbing agent is used in an amount (g) that depends on, for example, the size of the absorbent body (water absorbent article) and/or the intended absorption amount (in particular, the amount of urine absorption). The amount is 1 g or more, more preferably within a range of 5 to 30 g, particularly preferably within a range of 8 to 20 g, per absorbent body (water absorbent article).

The absorbent body can be easily produced by, for example, (i) blending the hydrophilic fiber, the particulate water absorbing agent, and as necessary any other fiber material and/or adhesive with one another or (ii) sandwiching the particulate water absorbing agent with a fiber material such as the above hydrophilic fiber.

The particulate water absorbing agent produced in the present invention, which has an excellent gel property, can be included in an absorbent body to provide an absorbent body that has a large absorption amount, that has a high liquid absorbing speed even at the second instance and later, and that has a low re-wet under pressure after liquid absorption.

Typical examples of the absorbent body of the present invention (that is, the water absorbent article as a finished product) include an absorbent body (water absorbent article) for urine absorption or blood absorption. Preferable examples include a child or adult disposable diaper, an incontinence pad, a sanitary napkin, a tampon, and a pet sheet. A particularly preferable example is a disposable diaper.

(E) Other Applications

The particulate water absorbing agent of the present invention, which has the above excellent water absorbent properties, can be used as a water-absorbing water retaining agent for any of various applications. Examples of such applications include water-absorbing water retaining agents for absorbent articles such as a disposable diaper, a sanitary napkin, an incontinence pad, and a medical pad, agriculture/ horticulture water retaining agents such as a soil modifying improving agent, a water retaining agent, and an agricultural chemical effect retaining agent, architectural water retaining agents such as an interior wall material condensation preventing agent and a cement additive, a release controlling agent, a refrigerating agent, a disposable body warmer, a sludge coagulating agent, a food freshness keeping agent, an ion-exchange column agent, a dehydrator for sludge or oil, a drying agent, a humidity controlling agent, and the like. The particulate water absorbing agent produced in the present invention is particularly suitably used in a sanitary material for absorption of feces, urine, or blood such as a disposable diaper and a sanitary napkin.

The present invention is not limited to the description of the embodiments above, but may be altered in various ways by a skilled person within the scope of the claims. Any embodiment based on a proper combination of technical means disclosed in different embodiments is also encompassed in the technical scope of the present invention. Further, combining different technical means disclosed in different embodiments can provide a new technical feature.

The present invention may also be arranged as below.

A particulate water absorbing agent of the present invention includes: a polyacrylic acid (salt)-based water absorbent resin as a main component, the particulate water absorbing agent having a swelling rate (CRC) of 32 to 45 g/g relative to 0.9-mass % saline, the particulate water absorbing agent including, at a proportion of 80 weight % or more, a particle having a size of 600 to 150 μm (as defined through a standard-sieve classification), the particulate water absorbing agent having a second-instance pure-water 50-fold swelling time (SST (in seconds)) of 70 seconds or less, a difference (DST=SST−FST) between a first-instance pure-water 50-fold swelling time (FST (in seconds)) and the second-instance pure-water 50-fold swelling time (SST (in seconds)) being +10 seconds or less.

The water absorbing agent of the present invention may preferably further include: a water-insoluble inorganic fine particle as a liquid permeability improving agent.

The water absorbing agent of the present invention may preferably be arranged such that the water-insoluble inorganic fine particle is contained in an amount of 0.05 to 5.0 mass %.

The water absorbing agent of the present invention may preferably be arranged such that the particulate water absorbing agent has a swelling rate under load (AAP 1.9 kPa) which swelling rate is 24 g/g or higher relative to 0.9-mass % saline.

The water absorbing agent of the present invention may preferably be arranged such that the water-insoluble inorganic particle is made of silicon dioxide.

The water absorbing agent of the present invention may preferably further include: as a liquid permeability improving agent for the water absorbing agent, a water-soluble polyhydric metal cation in an amount of 0.01 to 5.0 mass %.

The water absorbing agent of the present invention may preferably be arranged such that the water-soluble polyhydric metal cation is an aluminum cation.

The water absorbing agent of the present invention may preferably be arranged such that the DST is 0 seconds or less.

The water absorbing agent of the present invention may preferably be arranged such that the water absorbing agent includes, at 5 weight % or less, a particle that passes through a 150-μm mesh as defined with use of a standard sieve and/or includes, at 5 weight % or less, a particle that does not pass through a 710-μm mesh as defined with use of a standard sieve.

A method of the present invention for producing a water absorbing agent is a method for producing a particulate water absorbing agent, the method including a step of polymerization of a monomer aqueous solution including acrylic acid (salt) as a main component, a drying step, a pulverization step and/or classification step, a surface crosslinking step, and a liquid permeability improving agent adding step, the method including the steps of: (1) polymerization with the monomer aqueous solution having a monomer concentration of 30 mass % or more, the polymerization involving use of an internal crosslinking agent in an amount of 0.04 mol % or more relative to the monomer and producing a hydrogel; (2) drying the hydrogel, produced through the step (1), to produce a dried product having a swelling rate (CRC) of 35 to 55 g/g; (3) pulverizing the dried product into particles and/or classifying the particles to produce a water absorbent resin powder including, at 80 weight % or more relative to the entire water absorbent resin powder, a particle having a size of 600 to 150 μm; (4) adding a surface-crosslinking agent, which includes a compound containing a hydroxyl group and/or a derivative group thereof, to the water absorbent resin powder, produced through the step (3), to provide a swelling rate (CRC) of 3 to 15 g/g and a swelling rate (CRC) of 32 to 50 g/g to produce a surface-crosslinked water absorbent resin powder; and (5) adding a liquid permeability improving agent to the water absorbent resin powder simultaneously with the step (4) and/or to the surface-crosslinked water absorbent resin powder after the step (4).

The production method of the present invention may preferably be arranged such that the step (4) involves two or more kinds of organic compounds as the surface-crosslinking agent.

The production method of the present invention may preferably be arranged such that the step (5) involves adding, as the liquid permeability improving agent, a water-insoluble inorganic fine particle in an amount of 0.05 mass % to 5.0% mass relative to the water absorbing agent.

The production method of the present invention may preferably be arranged such that the water-insoluble inorganic particle is made of silicon dioxide.

The method of the present invention for producing a water absorbing agent may preferably be arranged such that the step (5) involves adding, as the liquid permeability improving agent, a compound containing a water-soluble polyhydric metal cation in an amount of 0.01 mass % to 5.0 mass % relative to the water absorbing agent.

The production method of the present invention may preferably be arranged such that the water-soluble polyhydric metal cation is an aluminum cation.

The production method of the present invention may preferably be arranged such that the water absorbent resin powder to be subjected to the step (4) includes, at 5 weight % or less, a particle that passes through a 150-μm mesh and/or includes, at 5 weight % or less, a particle that does not pass through a 710-μm mesh.

The production method of the present invention may preferably be arranged such that a first classification step is performed before the step (4); and a second classification step is performed after the step (4).

A water absorbent article of the present invention includes the particulate water absorbing agent of the present invention.

EXAMPLES

The description below deals in greater detail with the present invention on the basis of Examples and Comparative Examples. The present invention should, however, not be construed as being limited to the Examples. The physical properties of the particulate water absorbing agent, the water absorbent resin powder, the water absorbent resin particles, the water absorbing agent composition, and the water absorbent article produced in the present invention were measured at an air temperature of 25° C.±2° C. and a relative humidity of 50% RH unless otherwise specified.

(Method for Evaluating Particulate Water Absorbing Agent)

[Swelling Rate (CRC) for 0.9-Mass % Saline]

The swelling rate (CRC) for 0.9-mass % saline was measured according to Non Patent Literature 1 (ERT 441.2-02). The swelling rate (CRC) indicates an absorbency exhibited without pressure for 30 minutes relative to 0.9-mass % saline.

First, 0.200 g of the water absorbent resin or particulate water absorbing agent was put evenly in a bag of nonwoven fabric (85 mm×60 mm), and the bag was heat-sealed. The bag was then immersed in a large excess of 0.9-mass % saline (sodium chloride aqueous solution) at 25° C.±2° C. The bag was taken out 30 minutes later, drained in a centrifugal separator (available from KOKUSAN Corporation, a centrifuge model H-122) at 250 G for 3 minutes, and then measured for its mass W1 (g). Further, the same operation was conducted without use of the water absorbent resin or particulate water absorbing agent, and the bag for that operation was measured for its mass W0 (g). With reference to W1 and W0, the swelling rate (CRC) (g/g) was calculated on the basis of the following formula:

$$\text{Swelling rate (g/g)} = (W1(g) - W0(g))/(\text{mass (g) of water absorbent resin or particulate water absorbing agent}) - 1$$

[Swelling Rate Under Load (AAP) for 0.9-Mass % Saline]

The swelling rate under load (AAP) for 0.9-mass % saline was measured according to Non Patent Literature 2 (ERT 442.2-02). The swelling rate under load (AAP) indicates an absorbency exhibited at 1.9 kPa for 60 minutes relative to 0.9-mass % saline.

A 400-mesh metal gauze 2 of stainless steel (with a mesh size of 38 μm) was fused to the bottom of a plastic supporting cylinder having an inner diameter of 60 mm. Then, 0.900 g of the water absorbent resin or particulate water absorbing agent was spread out evenly on the metal gauze. On the water absorbent resin or particulate water absorbing agent, a piston and a load were placed in this order which were each slightly small in outer diameter than 60 mm with no gap between (i) the supporting cylinder and (ii) the piston or the load, which were not prevented from their vertical movement, and which were so adjusted as to be capable of applying a load of 1.9 kPa (0.3 psi) evenly on the water absorbent resin or particulate water absorbing agent as a test piece. This measuring device as a whole was measured for its mass Wa (g).

A glass filter with a diameter of 90 mm (available from Sougo Rikagaku Glass Seisakusho Co., Ltd., fine pore diameter: 100 to 120 μm) was placed in a petri dish having a diameter of 150 mm. Then, 0.9-mass % saline (25° C.±2° C.) was added in such an amount that the level of the 0.9-mass % saline was equal to the top surface of the glass filter. On the saline and the glass filter, a sheet of filter paper with a diameter of 90 mm (available from Advantec Toyo Kaisha, Ltd., product name: JIS P 3801 No. 2, with a thickness of 0.26 mm and a retaining particle diameter of 5 μm) was placed in such a manner that the entire surface of the sheet was wet. Further, an excess liquid was removed.

The whole measuring device described above was placed on the wet filter paper for absorption of the liquid under load. The whole measuring device was lifted up 1 hour later and measured for its mass Wb (g). With reference to Wa and Wb, the swelling rate under load (AAP) (g/g) was calculated on the basis of the following formula:

$$\text{Swelling rate under load (g/g)} = (Wb(g) - Wa(g))/(\text{mass (g) of water absorbent resin or water absorbing agent})$$

[First-Instance Pure-Water 50-Fold Swelling Time (FST or Swelling Time)]

[Second-Instance Pure-Water 50-Fold Swelling Time (SST or Second Swelling Time)]

See under "(A) Definitions of terms" above.

[Particle Size Distribution (Mass % of Particles with Sizes of 600 μm or Larger as Defined Through a Standard-Sieve Classification)]

The particle size distribution of the particulate water absorbing agent of the present invention was measured according to a method disclosed in European patent No. 1594556.

Specifically, 10.0 g of the particulate water absorbing agent was classified with use of JIS standard sieves (The IIDA TESTING SIEVE: inner diameter of 80 mm; JIS Z8801-1 (2000)) having respective mesh sizes of 850 μm, 710 μm, 600 μm, 500 μm, 425 μm, 300 μm, 212 μm, 150 μm, 106 μm, and 75 μm. After the classification, each sieve was measured for its weight, and the mass percentage (mass %) of particles with particle diameters of 600 μm to 150 μm was calculated. The term "mass percentage of particles with particle diameters of 600 μm or larger" refers to the mass proportion of the total amount of particles that remain on the JIS standard sieves having respective mesh sizes of 850 μm, 710 μm, and 600 μm relative to the entire particulate water absorbing agent.

[Degradable Soluble Component]

First, pH electrodes for use in measurement of a degradable soluble component were calibrated with use of pH standard buffer solutions (pH: 4.0, pH: 7.0, and pH: 10.0).

Next, 50 ml of physiological saline prepared in advance (0.9-mass % sodium chloride aqueous solution) was poured into a 100-ml glass beaker. Then, 0.1 N sodium hydroxide aqueous solution was dropped into the physiological saline while the physiological saline was being stirred with use of a stirrer chip (length of 30 mm×outer diameter of 8 mm) until the pH of the physiological saline reached 10. The titre (Vab [ml]) at this stage was measured as a blank. Subsequently, 0.1 N hydrochloric acid aqueous solution was dropped into the physiological saline while the physiological saline was being stirred until the pH of the physiological saline reached 2.7. The titre (Vbb [ml]) at this stage was measured also as a blank.

In addition, L-ascorbic acid was added to physiological saline prepared in advance until the concentration of L-ascorbic acid reached 0.05 mass %. This prepared a degradation test liquid. In other words, 0.5 g of L-ascorbic acid was dissolved in 999.5 g of physiological saline to prepare 1000.0 g of a degradation test liquid.

Then, 25 ml of the degradation test liquid was poured into a 250-ml polypropylene container having a lid, and 1.0 g of the water absorbing agent composition was added to the degradation test liquid to form a swollen gel. After that, the container was lidded to be sealed, and was let stand at 37° C. for 16 hours.

After the above operation (16 hours later), 175 ml of physiological saline was poured into the polypropylene container, and the mixture was stirred with use of a stirrer chip (length 30 mm×outer diameter of 8 mm) at a stirring speed of 500±50 rpm for 1 hour. This extracted a soluble component. This soluble component was then filtered through filter paper (available Toyo Roshi Kaisha, Ltd., No. 2/retaining particle diameter of 5 μm (defined by JIS P 3801)) to provide a filtrate.

Next, 20 ml (recorded as F [ml]) of the filtrate produced through the above operation was poured into a 100-ml glass beaker, and physiological saline was added to the filtrate for a total amount of 50 ml to provide a titration liquid. Even if the filtrate was less than 20 ml, the amount (F [ml]) was recorded, and physiological saline was added to the filtrate for a total amount of 50 ml to provide a titration liquid.

Then, 0.1 N sodium hydroxide aqueous solution was dropped into the titration liquid while the titration liquid was being stirred with use of a stirrer chip (length of 30 mm×outer diameter of 8 mm) until the pH of the titration liquid reached 10. The titre (Va[ml]) at this stage was measured. Subsequently, 0.1 N hydrochloric acid aqueous solution was dropped into the titration liquid while the titration liquid was being stirred until the pH of the titration liquid reached 2.7. The titre (Vb [ml]) at this stage was measured. With reference to these titres, the degradable soluble component was calculated on the basis of the following Formula (1):

$$\text{Degradable soluble component [mass \%]}=\{(Wa+Wb)/m)\} \times 100 \quad (1)$$

In Formula (1) above, Wa [g] indicates the relative mass of an acid group-containing unit in a soluble component of the water absorbing agent composition, and Wb [g] indicates the relative mass of a unit containing a carboxyl group (carboxylate) neutralized with a basic material in a soluble component of the water absorbing agent composition. These can be calculated on the basis of the following Formulae (2) and (3):

$$Wa[g]=Na \times 72 \times 200/F \quad (2)$$

$$Wb[g]=Nb \times 94 \times 200/F \quad (3)$$

Further, m [g] indicates the mass of the water absorbing agent composition.

In Formula (2) above, "72" indicates the mass per mole of a repeating unit of an acrylic acid polymer. In Formula (3) above, "94" indicates the mass per mole of a repeating unit of a sodium acrylate polymer. These values are, in the case where (i) a monomer containing an acid group other than acrylic acid has been copolymerized or (ii) potassium salt, lithium salt or the like, other than sodium salt, is used as alkali metal salt, calculated through appropriate conversion of the masses per mole of the above repeating units each into the average mass per mole of a repeating unit containing such another monomer or alkali metal salt.

In Formula (2) above, Na [mole] indicates the number of moles of the acid group in a soluble component contained in the titration liquid (filtrate). In Formula (3) above, Nb [mole] indicates the number of moles of the carboxyl group (carboxylate) neutralized with a basic material in a soluble component contained in the titration liquid (filtrate). These can be calculated on the basis of the following Formulae (4) and (5):

$$Na[\text{mole}]=\{(Va-Vab)/1000\} \times 0.1 \quad (4)$$

$$Nb[\text{mole}]=N_1-Na \quad (5)$$

In Formula (5), $N_1$ [mole] indicates the total number of moles of a soluble component contained in the titration liquid (filtrate), and can be calculated on the basis of the following Formula (6):

$$N_1 [\text{mole}]=\{(Vb-Vbb)/1000\} \times 0.1 \quad (6)$$

(Method for Evaluating Absorbent Body)

For evaluation of properties of an absorbent body including the particulate water absorbing agent of the present invention, an absorbent body below (particulate water absorbing agent having a concentration of 50 mass %) was prepared, and its absolute absorption amount, liquid absorbing times (the first instance, the second instance, and the third instance) as a multi-staged urination model, and re-wet were measured and evaluated.

[Method for Preparing Absorbent Body]

First, 50 g of the particulate water absorbing agent and 50 g of wood-ground pulp were dry-mixed with use of a mixer. The resulting mixture was then spread out on a 400-mesh wire screen (with a mesh size of 38 μm), and was formed into a web (sheet) of paper with use of air in a batch-type air paper making device. The basis weight was adjusted by adjusting the time of the air paper making. The web of paper was then cut into a rectangular shape (with a size of 120 mm×380 mm) to be molded. Next, this web was pressed under a pressure of 196.14 kPa (2 (kgf/cm²)) for 1 minute to provide an absorbent body in the form of a disposable diaper.

The absorbent body produced as above in the form of a disposable diaper contained 12 g of the particulate water absorbing agent, and had a core concentration of 50 mass % and a basis weight of approximately 526 (g/m²).

[Method for Producing Simulated Disposable Diaper as Absorbent Article]

The above absorbent body was placed on a back sheet (liquid impermeable sheet) made of liquid impermeable polypropylene and having a size of 120 mm×380 mm. Then, a sheet of nonwoven fabric having a size of 120 mm×380 mm was placed on the absorbent body, and a top sheet (liquid permeability sheet) made of liquid permeability polypropylene and having the same size as the sheet of nonwoven fabric was placed on the sheet of nonwoven fabric. This prepared a simulated child disposable diaper including four layers.

[Absolute Absorption Amount (g)]

The absorbent body (with a size of 120 mm×380 mm) was put into a bag of nonwoven fabric (with a size of 130 mm×400 mm), and the bag was heat-sealed. The bag was then immersed in 5 L of 0.9-mass % saline having a temperature adjusted to 25±3° C. The bag was taken out 30 minutes later, hung for 10 minutes to be drained, and measured for its weight (W3 (g)).

Further, a similar operation was conducted without use of the absorbent body, and the bag for that operation was measured for its weight (W4 (g)). The absolute absorption amount of the absorbent body was calculated on the basis of the following formula:

Absolute absorption amount (g)=$W3(g)-W4(g)$

[Liquid Absorbing Times (Seconds)]

An acrylic plate (with a size of 120 mm×380 mm) having a liquid inlet with a diameter of 70 mm at a central portion was placed on the above simulated disposable diaper. Then, an anchor was placed on the acrylic plate which anchor was adjusted to apply a load of 2.1 kPa evenly on the entire acrylic plate.

Next, 75 ml of 0.9-mass % saline was poured through the liquid inlet a total of three times at 30-minute intervals. The time needed for the poured saline to be absorbed by the simulated disposable diaper (that is, the time needed for the saline to be absorbed through the liquid permeability sheet) at the first instance, the second instance, and the third instance were recorded respectively as a first-instance liquid absorbing time, a second-instance liquid absorbing time, and a third-instance liquid absorbing time.

[Re-Wet (g)]

Following the above measurement of liquid absorbing times, 75 ml of saline was poured two more times (at 30-minute intervals) for a total of five times (with a total amount poured of 375 ml). The anchor and the acrylic plate were removed 30 minutes after the fifth pouring of saline. Then, 30 sheets of kitchen paper (with a size of 120 mm×380 mm, available from Oji Nepia Co., Ltd.), of which the total weight (W5 (g)) was measured in advance, were placed, and further, an acrylic plate (with a size of 120 mm×380 mm) and an anchor (total weight of 10 kg) that would apply a load evenly were placed quickly on the sheets of kitchen paper.

One minute later, the weight (W6 (g)) of the 30 sheets of kitchen paper was measured, and the re-wet (g) of the simulated disposable diaper was calculated on the basis of the following formula:

Re-wet(g)=$W6$(g)−$W5$(g)

[Diffusion Distance (%)]

Following the measurement of re-wet, the top sheet of the simulated disposable diaper was visually checked for measurement of the distance of saline diffused in the long-side direction as L (mm). The diffusion distance (%) was calculated on the basis of the following formula:

Diffusion distance (%)=$L$(mm)÷380 (mm)×100

Production Example 1

First, into a reactor including a stainless steel kneader, a lid attached to the kneader, and a jacket, the kneader being a double-arm kneader having an internal volume of 10 L and two sigma blades, (i) 335.7 g of acrylic acid, (ii) 3552.2 g of a 37-mass % sodium acrylate aqueous solution, (iii) 1074.17 g of pure water, and (iv) 4.39 g (0.045 mol %) of polyethyleneglycol diacrylate (with a molecular weight of 523) were poured to prepare a reaction liquid (with a monomer concentration of 33 mass %). The reactor was then deaerated in a nitrogen gas atmosphere for 20 minutes.

After that, 22.36 g of a 10-mass % sodium persulfate aqueous solution and 11.18 g of a 0.1-mass % L-ascorbic acid aqueous solution were separately added to the reaction liquid while the reaction liquid was being stirred. Approximately 25 seconds later, polymerization started. The produced water-containing gel-like crosslinked polymer was polymerized at 25 to 95° C. while being crushed. Then, 30 minutes after the start of the polymerization, the water-containing gel-like crosslinked polymer was taken out from the reactor. The water-containing gel-like crosslinked polymer produced had grains each refined to have a diameter of approximately 5 mm or smaller.

The refined water-containing gel-like crosslinked polymer was spread out on a metal gauze having a mesh size of 300 μm (50 mesh), dried with hot air at 180° C. for 50 minutes, pulverized with use of a roll mill, classified with use of a JIS standard sieve having a mesh size of 850 μm and a JIS standard sieve having a mesh size of 150 μm, and then blended. This operation produced water absorbent resin particles (1).

Production Example 2

A solution (A) prepared by mixing 246.16 g of acrylic acid, 0.840 g (0.047 mol %) of polyethyleneglycol diacrylate (with a molecular weight of 523), and 1.51 g of a 1.0-mass % diethylene triamine pentaacetate pentasodium aqueous solution with one another was poured into a 1-L polypropylene container having an inner diameter of 80 mm and covered with styrene foam (heat insulating material), and was stirred with use of a magnetic stirrer, while a solution (B) prepared by mixing 205.67 g of a 48.5-mass % sodium hydroxide aqueous solution and 232.16 g of pure water having a temperature adjusted to 50° C. was added quickly in an open system to the solution (A) to be mixed. This prepared a monomer aqueous solution (with a monomer concentration of 43 mass %). The temperature of this monomer aqueous solution was raised to approximately 100° C. due to heat of neutralization and heat of solution.

Next, 13.66 g of a 3.0-mass % sodium persulfate aqueous solution was added to the monomer aqueous solution while being stirred. Immediately after that, the mixture was poured under atmospheric pressure into a stainless steel butt vessel (with a bottom surface of 250×250 mm, a top surface of 640×640 mm, and a height of 50 mm; central cross section: trapezoidal; inner surface provided with Teflon (®) attached thereto). The butt vessel was heated with use of a hot plate (available from Iuchi Seiei Do Ltd., NEO HOTPLATE HI-1000) until its surface temperature reached 100° C.

Soon after the monomer aqueous solution was poured into the butt vessel, a polymerization reaction started. This polymerization reaction proceeded with steam being generated and the mixture foaming and swelling in various directions. The mixture was then shrunk to a size slightly larger than the size of the butt vessel. This swelling and shrinking ended within approximately 1 minute. Then, 4 minutes after the start of the polymerization reaction, the water-containing gel polymer (hydrogel) was taken out.

The hydrogel produced through the polymerization reaction was crushed with use of a meat chopper (ROYAL MEAT-CHOPPER VR400K, available from Iizuka Kogyo Co., Ltd./with a die diameter of 9.5 mm). This operation produced a water-containing gel-like crosslinked polymer having refined grains.

The refined water-containing gel-like crosslinked polymer was spread out on a metal gauze having a mesh size of 300 μm (50 mesh), dried with hot air at 180° C. for 50 minutes, pulverized with use of a roll mill, classified with use of a JIS standard sieve having a mesh size of 850 μm and a JIS standard sieve having a mesh size of 150 μm, and then blended. This operation produced water absorbent resin particles (2).

Production Example 3

An operation similar to Production Example 2 was conducted except that polyethyleneglycol diacrylate (with a molecular weight of 523) was used in a different amount of 0.715 g (0.04 mol %). This operation produced water absorbent resin particles (3).

Production Example 4

An operation similar to Production Example 1 was conducted except that polyethyleneglycol diacrylate (with a molecular weight of 523) was replaced with trimethylolpropane triacrylate (with a molecular weight of 296) in an amount of 2.76 g (0.05 mol %). This operation produced water absorbent resin particles (4).

Production Example 5

An operation similar to Production Example 1 was conducted except that polyethyleneglycol diacrylate (with a molecular weight of 523) was replaced with trimethylolpropane triacrylate (with a molecular weight of 296) in an amount of 2.37 g (0.043 mol %). This operation produced water absorbent resin particles (5).

Production Example 6

An operation similar to Production Example 1 was conducted except that the reaction liquid was a mixture of 386.5 g of acrylic acid, 4090.5 g of a 37-mass % sodium acrylate aqueous solution, 492.05 g of pure water, and 3.93 g (0.035 mol %) of polyethyleneglycol diacrylate (with a molecular weight of 523). This operation produced water absorbent resin particles (6) from a monomer having a concentration of 38%.

Production Example 7

An operation similar to Production Example 2 was conducted except that the reaction liquid was a mixture of 257.61 g of acrylic acid, 0.505 g (0.027 mol %) of polyethyleneglycol diacrylate (with a molecular weight of 523), 215.24 g of a 48.5-mass % sodium hydroxide aqueous solution, and 210.77 g of pure water. This operation produced water absorbent resin particles (7) from a monomer having a concentration of 45%.

Production Example 8

An operation similar to Production Example 1 was conducted except that the reaction liquid was a mixture of 386.5 g of acrylic acid, 4090.5 g of a 37-mass % sodium acrylate aqueous solution, 480.24 g of pure water, and 4.15 g (0.037 mol %) of polyethyleneglycol diacrylate (with a molecular weight of 523). This operation produced water absorbent resin particles (8) from a monomer having a concentration of 38%.

Production Example 9

An operation similar to Production Example 1 was conducted except that the reaction liquid was a mixture of 386.5 g of acrylic acid, 4090.5 g of a 37-mass % sodium acrylate aqueous solution, 482.60 g of pure water, and 1.80 g (0.016 mol %) of polyethyleneglycol diacrylate (with a molecular weight of 523). This operation produced water absorbent resin particles (9) from a monomer having a concentration of 38%.

Production Example 10

An operation similar to Production Example 2 was conducted except that the reaction liquid was a mixture of 257.61 g of acrylic acid, 0.337 g (0.018 mol %) of polyethyleneglycol diacrylate (with a molecular weight of 523), 215.24 g of a 48.5-mass % sodium hydroxide aqueous solution, and 210.94 g of pure water. This operation produced water absorbent resin particles (10) from a monomer having a concentration of 45%.

Production Example 11

An operation similar to Production Example 1 was conducted except that the reaction liquid was a mixture of 386.5 g of acrylic acid, 4090.5 g of a 37-mass % sodium acrylate aqueous solution, 482.30 g of pure water, and 2.10 g (0.033 mol %) of trimethylolpropane triacrylate (with a molecular weight of 296). This operation produced water absorbent resin particles (11) from a monomer having a concentration of 38%.

Production Example 12

An operation similar to Production Example 1 was conducted except that the reaction liquid was a mixture of 386.5 g of acrylic acid, 4090.5 g of a 37-mass % sodium acrylate aqueous solution, 482.81 g of pure water, and 1.59 g (0.025 mol %) of trimethylolpropane triacrylate (with a molecular weight of 296). This operation produced water absorbent resin particles (11) from a monomer having a concentration of 38%.

Production Example 13

An operation similar to Production Example 2 was conducted except that the reaction liquid was a mixture of 257.61 g of acrylic acid, 1.683 g (0.09 mol %) of polyethyleneglycol diacrylate (with a molecular weight of 523), 215.24 g of a 48.5-mass % sodium hydroxide aqueous solution, and 209.60 g of pure water. This operation produced water absorbent resin particles (13) from a monomer having a concentration of 43%.

Production Example 14

An operation similar to Production Example 2 was conducted except that the reaction liquid was a mixture of 257.61 g of acrylic acid, 1.215 g (0.065 mol %) of polyethyleneglycol diacrylate (with a molecular weight of 523), 215.24 g of a 48.5-mass % sodium hydroxide aqueous solution, and 210.06 g of pure water. This operation produced water absorbent resin particles (14) from a monomer having a concentration of 43%.

Production Example 15

An operation similar to Production Example 1 was conducted except that the blending for the particle size was so adjusted that 28 mass % of all particles were 600 μm or larger in size. This operation produced water absorbent resin particles (15).

Production Example 16

An operation similar to Production Example 2 was conducted except that the blending for the particle size was so adjusted that 23 mass % of all particles were 600 μm or larger in size. This operation produced water absorbent resin particles (16).

Production Example 17

An operation similar to Production Example 1 was conducted except that it used (i) acrylic acid in an amount of 203.4 g, (ii) a 37-mass % sodium acrylate aqueous solution in an amount of 2152.8 g, (iii) pure water in an amount of 2620.2 g (with a monomer concentration of 20 mass %), (iv) polyethyleneglycol diacrylate (with a molecular weight of 523) in an amount of 8.83 g (0.145 mol %), (v) a 10-mass % sodium persulfate aqueous solution in an amount of 12.6 g, and (vi) a 0.1-mass % L-ascorbic acid aqueous solution in an amount of 2.71 g. This operation produced water absorbent resin particles (17).

Production Example 18

An operation similar to Production Example 2 was conducted except that it used (i) acrylic acid in an amount of 172.47 g, (ii) polyethyleneglycol diacrylate (with a molecular weight of 523) in an amount of 4.378 g (0.105 mol %), (iii) a 1.0-mass % diethylene triamine pentaacetate pentasodium aqueous solution in an amount of 1.05 g, (iv) a 48.5-mass % sodium hydroxide aqueous solution in an amount of 140.75 g, (v) pure water in an amount of 371.78 g (with a monomer concentration of 25 mass %), and (vi) a 3.0-mass % sodium persulfate aqueous solution in an amount of 9.57 g. This operation produced water absorbent resin particles (18).

Example 1

A surface crosslinking treatment was performed by (i) evenly mixing, with 100 parts by mass of the water absorbent resin particles (1) produced in Production Example 1, a surface-crosslinking agent aqueous solution prepared from 0.5 part by mass of propylene glycol, 0.3 part by mass of 1,4-butandiol, 0.03 part by mass of ethyleneglycol diglycidyl ether, and 3.0 parts by mass of pure water and (ii) heat-treating the mixture at 210° C. for 35 minutes. This operation produced a surface-crosslinked water absorbent resin powder (1). The above heat treatment was performed by stirring the mixture in a stainless steel container immersed in an oil bath.

Next, to 100 parts by mass of the resulting water absorbent resin powder (1), a liquid mixture of 1.0 part by mass of a 27.5-mass % aluminum sulfate aqueous solution, 0.17 part by mass of a 60-mass % sodium lactate aqueous solution, and 0.025 part by mass of propylene glycol was added as water-soluble polyhydric metal cations. The resulting mixture was dried at 60° C. for 1 hour with no air flow. Further, 0.5 part by mass of Reolosil QS-20 (hydrophilic amorphous silica, available from TOKUYAMA) was mixed evenly as water-insoluble inorganic fine particles. This operation produced a water absorbent resin as a water absorbing agent (1), which contained 63 mass % of a degradable soluble component.

Example 2

An operation similar to Example 1 was conducted except that the water absorbent resin particles (1) were replaced with the water absorbent resin particles (2). This operation produced a water absorbing agent (2).

Example 3

An operation similar to Example 1 was conducted except that the water absorbent resin particles (1) were replaced with the water absorbent resin particles (3) and that the surface crosslinking treatment involved adding, to 100 parts by mass of the water absorbent resin particles (3), a surface-crosslinking agent aqueous solution including 0.6 part by mass of propylene glycol, 0.4 part by mass of ethylene carbonate, 0.03 part by mass of ethyleneglycol diglycidyl ether, and 3.0 parts by mass of pure water. This operation produced a water absorbing agent (3).

Example 4

An operation similar to Example 2 was conducted except that the heat treatment for surface crosslinking was performed for 25 minutes, that no water-soluble polyhydric metal cations were added, and that 0.3 part by mass of Aerosil 200 (hydrophilic amorphous silica, available from Nippon Aerosil Co., Ltd.) was added as water-insoluble inorganic fine particles. This operation produced a water absorbing agent (4), which contained 58 mass % of a degradable soluble component.

Example 5

An operation similar to Example 1 was conducted except that the heat treatment for surface crosslinking was performed for 25 minutes and that 0.5 part by mass of Aerosil 200 (hydrophilic amorphous silica, available from Nippon Aerosil Co., Ltd.) was added as water-insoluble inorganic fine particles. This operation produced a water absorbing agent (5).

Example 6

An operation similar to Example 1 was conducted except that the water absorbent resin particles (1) were replaced with the water absorbent resin particles (4), that no water-soluble polyhydric metal cations were added, and that 0.2 part by mass of Aerosil 200 (hydrophilic amorphous silica, available from Nippon Aerosil Co., Ltd.) was added as water-insoluble inorganic fine particles. This operation produced a water absorbing agent (6).

Example 7

An operation similar to Example 1 was conducted except that the water absorbent resin particles (1) were replaced with the water absorbent resin particles (5), that the surface crosslinking treatment involved adding, to 100 parts by mass of the water absorbent resin particles (5), a surface-crosslinking agent aqueous solution including 0.6 part by mass of propylene glycol, 0.4 part by mass of ethylene carbonate, 0.03 part by mass of ethyleneglycol diglycidyl ether, and 3.0 parts by mass of pure water, that no water-soluble polyhydric metal cations were added, and that 1.0 part by mass of Aerosil 200 (hydrophilic amorphous silica, available from Nippon Aerosil Co., Ltd.) was added as water-insoluble inorganic fine particles. This operation produced a water absorbing agent (7).

Comparative Example 1

An operation similar to Example 1 was conducted except that the water absorbent resin particles (1) were replaced with the water absorbent resin particles (6). This operation produced a comparative water absorbing agent (1).

Comparative Example 2

An operation similar to Example 1 was conducted except that the water absorbent resin particles (1) were replaced with the water absorbent resin particles (7) and that the surface crosslinking treatment involved adding, to 100 parts by mass of the water absorbent resin particles (7), a surface-crosslinking agent aqueous solution including 0.6 part by mass of propylene glycol, 0.4 part by mass of ethylene carbonate, 0.03 part by mass of ethyleneglycol diglycidyl ether, and 3.0 parts by mass of pure water. This operation produced a comparative water absorbing agent (2).

Comparative Example 3

An operation similar to Example 1 was conducted except that the water absorbent resin particles (1) were replaced with the water absorbent resin particles (8), that no water-soluble polyhydric metal cations were added, and that the water-insoluble inorganic fine particles were added in an amount of not 0.5 part by mass but 0.3 part by mass. This operation produced a comparative water absorbing agent (3).

Comparative Example 4

An operation similar to Example 1 was conducted except that the water absorbent resin particles (1) were replaced with the water absorbent resin particles (9), that no water-soluble polyhydric metal cations were added, and that the water-insoluble inorganic fine particles were added in an amount of 0.3 part by mass. This operation produced a comparative water absorbing agent (4).

Comparative Example 5

An operation similar to Example 1 was conducted except that the water absorbent resin particles (1) were replaced with the water absorbent resin particles (10), that the heat treatment for surface crosslinking was performed for 25 minutes, that no water-soluble polyhydric metal cations were added, and that 0.5 part by mass of Aerosil 200 (hydrophilic amorphous silica, available from Nippon Aerosil Co., Ltd.) was added as water-insoluble inorganic fine particles. This operation produced a comparative water absorbing agent (5).

Comparative Example 6

An operation similar to Example 1 was conducted except that the water absorbent resin particles (1) were replaced with the water absorbent resin particles (11) and that 0.2 part by mass of Aerosil 200 (hydrophilic amorphous silica, available from Nippon Aerosil Co., Ltd.) was added as water-insoluble inorganic fine particles. This operation produced a comparative water absorbing agent (6).

Comparative Example 7

An operation similar to Example 1 was conducted except that the water absorbent resin particles (1) were replaced with the water absorbent resin particles (12), that no water-soluble polyhydric metal cations were added, and that 0.5 part by mass of Aerosil 200 (hydrophilic amorphous silica, available from Nippon Aerosil Co., Ltd.) was added as water-insoluble inorganic fine particles. This operation produced a comparative water absorbing agent (7).

Comparative Example 8

An operation similar to Example 1 was conducted except that neither water-soluble polyhydric metal cations nor water-insoluble inorganic fine particles were added. This operation produced a comparative water absorbing agent (8).

Comparative Example 9

An operation similar to Example 1 was conducted except that the water absorbent resin particles (1) were replaced with the water absorbent resin particles (4) and that no water-insoluble inorganic fine particles were added. This operation produced a comparative water absorbing agent (9).

Comparative Example 10

An operation similar to Example 1 was conducted except that the water absorbent resin particles (1) were replaced with the water absorbent resin particles (13), that the surface crosslinking treatment involved adding, to 100 parts by mass of the water absorbent resin particles (13), a surface-crosslinking agent aqueous solution including 0.6 part by mass of propylene glycol, 0.4 part by mass of ethylene carbonate, 0.03 part by mass of ethyleneglycol diglycidyl ether, and 3.0 parts by mass of pure water, and that no water-insoluble inorganic fine particles were added. This operation produced a comparative water absorbing agent (10).

Comparative Example 11

An operation similar to Example 1 was conducted except that the water absorbent resin particles (1) were replaced with the water absorbent resin particles (14) and that no water-insoluble inorganic fine particles were added. This operation produced a comparative water absorbing agent (11).

Comparative Example 12

An operation similar to Example 1 was conducted except that the water absorbent resin particles (1) were replaced with the water absorbent resin particles (15). This operation produced a comparative water absorbing agent (12).

Comparative Example 13

An operation similar to Example 4 was conducted except that the water absorbent resin particles (2) were replaced with the water absorbent resin particles (16). This operation produced a comparative water absorbing agent (13).

Comparative Example 14

An operation similar to Example 1 was conducted except that the water absorbent resin particles (1) were replaced with the water absorbent resin particles (17). This operation produced a comparative water absorbing agent (14).

Comparative Example 15

An operation similar to Example 2 was conducted except that the water absorbent resin particles (2) were replaced with the water absorbent resin particles (18). This operation produced a comparative water absorbing agent (15).

Comparative Example 16

In Example 1, particles with sizes of 600 µm or larger and particles with sizes of 300 µm or less of the water absorbent resin powder (1) after the surface crosslinking treatment were removed through a standard-sieve classification. Then, an additive was added as in Example 1. This operation produced a comparative water absorbing agent (16).

Comparative Example 17

In Example 4, particles with sizes of 600 μm or larger and particles with sizes of 300 μm or less of the water absorbent resin powder (2) after the surface crosslinking treatment were removed through a standard-sieve classification. Then, an additive was added as in Example 4. This operation produced a comparative water absorbing agent (17).

Example 8

In Example 1, a surface crosslinking treatment was performed which involved (i) evenly mixing, with 100 parts by mass of the water absorbent resin particles (1), a surface-crosslinking agent aqueous solution prepared of 0.7 part by mass of propylene glycol, 0.6 part by mass of ethylene carbonate, 0.03 part by mass of ethyleneglycol diglycidyl ether, and 2.0 parts by mass of pure water and (ii) heat-treating the mixture at 200° C. for 40 minutes. This operation produced a surface-crosslinked water absorbent resin powder (8). An operation similar to Example 1 was conducted except that to 100 parts by mass of the water absorbent resin powder (8) produced, a liquid mixture of 0.5 part by mass of a 27.5-mass % aluminum sulfate aqueous solution, 0.2 part by mass of a 60-mass % sodium lactate aqueous solution, 0.03 part by mass of propylene glycol, and 0.044 part by mass of a 45-mass % diethylene triamine pentaacetate pentasodium was added as water-soluble polyhydric metal cations. This operation produced a water absorbent resin as a water absorbing agent (8), which contained 16 mass % of a degradable soluble component.

Example 9

In Example 4, a surface crosslinking treatment was performed which involved (ii) evenly mixing, with 100 parts by mass of the water absorbent resin particles (1), a surface-crosslinking agent aqueous solution prepared of 0.7 part by mass of propylene glycol, 0.25 part by mass of 1,4-butandiol, 0.03 part by mass of ethyleneglycol diglycidyl ether, and 2.5 parts by mass of pure water and (ii) heat-treating the mixture at 210° C. for 40 minutes. This operation produced a surface-crosslinked water absorbent resin powder (9).

An operation similar to Example 4 was conducted except that to 100 parts by mass of the water absorbent resin powder (9) produced, a liquid mixture of 1.2 parts by mass of pure water and 0.044 part by mass of a 45-mass % diethylene triamine pentaacetate pentasodium was added. This operation produced a water absorbent resin as a water absorbing agent (9), which contained 58 mass % of a degradable soluble component.

Table 1 shows, for each of the water absorbing agents (1) to (9) and comparative water absorbing agents (1) to (17) produced, (i) the concentration (mass %) of the monomer for production of the water absorbent resin particles, (ii) the kind and amount used (mol %) of the internal crosslinking agent, and (iii) the particle size distribution (mass %) of the water absorbent resin particles before surface crosslinking.

The phrase "600 μm on amount (mass %)" refers to the "mass percentage of particles with particle diameters of 600 μm or larger" described under [Particle size distribution (mass % of particles with sizes of 600 μm or larger as defined through a standard-sieve classification)] above. The table shows "PEGDA" and "TMPTA", which stand for polyethyleneglycol diacrylate and trimethylolpropane triacrylate, respectively.

Table 2 shows the correspondence between the water absorbing agents shown in Table 1 and water absorbent resin particles used to produce those water absorbing agents.

TABLE 1

|     |    | WA    | Monomer concentration (mass %) | Internal crosslinking agent Agent kind | Internal crosslinking agent Amount (mol %) | 600 μm on amount (mass %) | 150 μm pass amount (mass %) | 600 to 150 μm amount (mass %) | 710 μm on amount (mass %) | D50 (μm) |
|-----|----|-------|-------|-------|-------|-----|-----|-----|-----|-----|
| EX  | 1  | WA 1  | 33    | PEGDA | 0.045 | 8   | 2   | 90  | 1   | 380 |
|     | 2  | WA 2  | 43    | PEGDA | 0.047 | 9   | 2   | 89  | 1   | 420 |
|     | 3  | WA 3  | 43    | PEGDA | 0.04  | 12  | 1   | 87  | 1   | 440 |
|     | 4  | WA 4  | 43    | PEGDA | 0.047 | 9   | 2   | 89  | 1   | 420 |
|     | 5  | WA 5  | 33    | PEGDA | 0.045 | 8   | 2   | 90  | 1   | 380 |
|     | 6  | WA 6  | 33    | TMPTA | 0.05  | 16  | 1   | 83  | 3   | 470 |
|     | 7  | WA 7  | 33    | TMPTA | 0.043 | 8   | 2   | 90  | 1   | 380 |
|     | 8  | WA 8  | 33    | PEGDA | 0.045 | 8   | 2   | 90  | 1   | 380 |
|     | 9  | WA 9  | 43    | PEGDA | 0.047 | 9   | 2   | 89  | 1   | 420 |
| CEX | 1  | CWA 1 | 38    | PEGDA | 0.035 | 8   | 2   | 90  | 1   | 380 |
|     | 2  | CWA 2 | 45    | PEGDA | 0.027 | 11  | 1   | 88  | 2   | 430 |
|     | 3  | CWA 3 | 38    | PEGDA | 0.037 | 10  | 1   | 89  | 1   | 430 |
|     | 4  | CWA 4 | 38    | PEGDA | 0.016 | 11  | 1   | 88  | 2   | 430 |
|     | 5  | CWA 5 | 45    | PEGDA | 0.018 | 23  | 0   | 77  | 7   | 510 |
|     | 6  | CWA 6 | 38    | TMPTA | 0.033 | 9   | 2   | 89  | 1   | 420 |
|     | 7  | CWA 7 | 38    | TMPTA | 0.025 | 7   | 2   | 91  | 0   | 380 |
|     | 8  | CWA 8 | 33    | PEGDA | 0.045 | 8   | 2   | 90  | 1   | 380 |
|     | 9  | CWA 9 | 33    | TMPTA | 0.05  | 16  | 1   | 83  | 3   | 470 |
|     | 10 | CWA 10| 45    | PEGDA | 0.09  | 20  | 1   | 79  | 6   | 490 |
|     | 11 | CWA 11| 45    | PEGDA | 0.065 | 17  | 1   | 82  | 5   | 470 |
|     | 12 | CWA 12| 33    | PEGDA | 0.045 | 28  | 0   | 72  | 10  | 530 |
|     | 13 | CWA 13| 43    | PEGDA | 0.047 | 25  | 1   | 74  | 8   | 520 |
|     | 14 | CWA 14| 20    | PEGDA | 0.145 | 8   | 2   | 90  | 1   | 380 |
|     | 15 | CWA 15| 25    | PEGDA | 0.105 | 9   | 2   | 89  | 1   | 420 |

TABLE 1-continued

| | WA | Monomer concentration (mass %) | Internal crosslinking agent Agent kind | Internal crosslinking agent Amount (mol %) | 600 μm on amount (mass %) | 150 μm pass amount (mass %) | 600 to 150 μm amount (mass %) | 710 μm on amount (mass %) | D50 (μm) |
|---|---|---|---|---|---|---|---|---|---|
| 16 | CWA 16 | 33 | PEGDA | 0.045 | 0 | 0 | 100 | 0 | 410 |
| 17 | CWA 17 | 43 | PEGDA | 0.047 | 0 | 0 | 100 | 0 | 410 |

"EX" stands for "Example".
"CEX" stands for "Comparative Example".
"WA" stands for "water absorbing agent".
"CWA" stands for "comparative water absorbing agent".

TABLE 2

| | | Kind of WA | WP used to produce WA |
|---|---|---|---|
| EX | 1 | WA 1 | WP (1) |
| | 2 | WA 2 | WP (2) |
| | 3 | WA 3 | WP (3) |
| | 4 | WA 4 | WP (2) |
| | 5 | WA 5 | WP (1) |
| | 6 | WA 6 | WP (4) |
| | 7 | WA 7 | WP (5) |
| | 8 | WA 8 | WP (1) |
| | 9 | WA 9 | WP (2) |
| CEX | 1 | CWA 1 | WP (6) |
| | 2 | CWA 2 | WP (7) |
| | 3 | CWA 3 | WP (8) |
| | 4 | CWA 4 | WP (9) |
| | 5 | CWA 5 | WP (10) |
| | 6 | CWA 6 | WP (11) |
| | 7 | CWA 7 | WP (12) |
| | 8 | CWA 8 | WP (1) |
| | 9 | CWA 9 | WP (4) |
| | 10 | CWA 10 | WP (13) |
| | 11 | CWA 11 | WP (14) |
| | 12 | CWA 12 | WP (15) |
| | 13 | CWA 13 | WP (16) |
| | 14 | CWA 14 | WP (17) |
| | 15 | CWA 15 | WP (18) |
| | 16 | CWA 16 | WP (1) |
| | 17 | CWA 17 | WP (2) |

"EX" stands for "Example".
"CEX" stands for "Comparative Example".
"WA" stands for "water absorbing agent".
"CWA" stands for "comparative water absorbing agent".
"WP" stands for "Water absorbent resin particles".

Table 3 shows, for each of the water absorbing agents (1) to (9) and comparative water absorbing agents (1) to (13) produced, the results of measurements of the CRC, AAP, FST, SST, DST, and particle size distribution of the water absorbing agent.

TABLE 3

| | | WA | CRC (g/g) | AAP (g/g) | FST (sec) | SST (sec) | DST (sec) | 600 μm on AM (m %) | 150 μm pass AM (m %) | 600 to 150 μm AM (m %) | 710 μm on AM (m %) | D50 (μm) |
|---|---|---|---|---|---|---|---|---|---|---|---|---|
| EX | 1 | WA 1 | 34 | 29 | 67 | 62 | −5 | 8 | 1 | 91 | 1 | 390 |
| | 2 | WA 2 | 34 | 30 | 61 | 58 | −3 | 10 | 1 | 89 | 2 | 440 |
| | 3 | WA 3 | 34 | 29 | 64 | 61 | −3 | 12 | 0 | 88 | 1 | 450 |
| | 4 | WA 4 | 37 | 28 | 40 | 41 | 1 | 10 | 1 | 89 | 2 | 440 |
| | 5 | WA 5 | 36 | 27 | 63 | 53 | −10 | 8 | 1 | 91 | 1 | 390 |
| | 6 | WA 6 | 32 | 30 | 43 | 43 | 0 | 16 | 0 | 84 | 4 | 480 |
| | 7 | WA 7 | 33 | 27 | 45 | 38 | −7 | 8 | 1 | 91 | 1 | 390 |
| | 8 | WA 8 | 33 | 30 | 64 | 62 | −2 | 8 | 1 | 91 | 1 | 390 |
| | 9 | WA 9 | 35 | 29 | 43 | 40 | −3 | 10 | 1 | 89 | 2 | 440 |
| CEX | 1 | CWA 1 | 34 | 27 | 69 | 72 | 3 | 8 | 1 | 91 | 1 | 390 |
| | 2 | CWA 2 | 34 | 26 | 61 | 91 | 30 | 11 | 0 | 89 | 3 | 440 |
| | 3 | CWA 3 | 34 | 27 | 45 | 92 | 47 | 10 | 0 | 90 | 2 | 440 |
| | 4 | CWA 4 | 38 | 26 | 36 | 95 | 59 | 11 | 0 | 89 | 3 | 440 |
| | 5 | CWA 5 | 42 | 18 | 61 | 108 | 47 | 23 | 0 | 77 | 9 | 520 |
| | 6 | CWA 6 | 35 | 26 | 62 | 71 | 9 | 10 | 1 | 89 | 2 | 440 |
| | 7 | CWA 7 | 37 | 25 | 55 | 91 | 36 | 8 | 1 | 91 | 1 | 390 |
| | 8 | CWA 8 | 34 | 30 | 43 | 58 | 15 | 8 | 1 | 91 | 1 | 390 |
| | 9 | CWA 9 | 33 | 29 | 48 | 65 | 17 | 16 | 0 | 84 | 4 | 480 |
| | 10 | CWA 10 | 27 | 27 | 44 | 26 | −18 | 20 | 0 | 80 | 8 | 510 |
| | 11 | CWA 11 | 29 | 26 | 45 | 50 | 5 | 18 | 0 | 82 | 7 | 490 |

TABLE 3-continued

| | WA | CRC (g/g) | AAP (g/g) | FST (sec) | SST (sec) | DST (sec) | 600 μm on AM (m %) | 150 μm pass AM (m %) | 600 to 150 μm AM (m %) | 710 μm on AM (m %) | D50 (μm) |
|---|---|---|---|---|---|---|---|---|---|---|---|
| 12 | CWA 12 | 34 | 29 | 68 | 68 | 0 | 29 | 0 | 71 | 13 | 550 |
| 13 | CWA 13 | 37 | 28 | 48 | 51 | 3 | 26 | 0 | 74 | 10 | 540 |

"EX" stands for "Example".
"CEX" stands for "Comparative Example".
"WA" stands for "water absorbing agent".
"CWA" stands for "comparative water absorbing agent".
"AM" stands for "amount".
"m %" stands for "mass %".

(Recap)

As shown in Table 3, the particulate water absorbing agent of the present invention is a novel water absorbing agent that not only has a high water absorption capacity (CRC) of 32 g/g or more and includes 600 μm-on particles in only a small amount of 20 mass % or less, but also (i) has a second-instance water absorbing speed (SST) of only 70 seconds or less (for a hydrogel swollen once to further absorb water), which had not been considered at all, and (ii) has a second-instance pure-water 50-fold swelling time (SST (in seconds)) that is not longer than the first-instance pure-water 50-fold swelling time (FST (in seconds)) by 10 seconds or longer, or SST−FST≤10 seconds (the SST was conventionally much longer). The particulate water absorbing agent of the present invention additionally has a high water absorption capacity under load AAP of 24 g/g or higher.

The inventors of the present invention have found that conventional water absorbing agents (comparative water absorbing agents) may, in contrast to the particulate water absorbing agent of the present invention, have a second-instance pure-water 50-fold swelling time (SST) of longer than 70 seconds (Comparative Examples 1 to 4 and Comparative Examples 5 to 7) or have a SST longer than the FST by longer than 10 seconds (Comparative Examples 2 to 5 and Comparative Examples 7 to 9) and that such conventional water absorbing agents are insufficient in absorption when used in diapers described below (in particular, multi-staged urination). The inventors of the present invention have further found that even Comparative Examples 12 and 13, which had conventional particle sizes (850-150 μm as defined through a standard-sieve classification), are insufficient in absorption when used in diapers described below (in particular, multi-staged urination). In addition, reducing the second-instance pure-water 50-fold swelling time (SST (in seconds)) will require reducing the water absorption capacity CRC to 27 g/g as in Comparative Example 10. Such a water absorbing agent will be insufficient in absorption when used in a diaper described below (in particular, multi-staged urination).

(Example 10) to (Example 13)

The water absorbing agents (1), (2), (4), and (6) were used to produce absorbent bodies described above and simulated disposable diapers as absorbent articles. The absorbent bodies produced (each containing 12 g or 50 mass % of the particulate water absorbing agent) were referenced as absorbent bodies (1), (2), (3), and (4). The simulated disposable diapers produced were referenced as simulated disposable diapers (1), (2), (3), and (4).

(Comparative Example 18) to (Comparative Example 23)

The comparative water absorbing agents (1), (5), (7), (8), (10), and (11) were used to produce absorbent bodies described above and simulated disposable diapers as absorbent articles. The absorbent bodies produced (each containing 12 g or 50 mass % of the particulate water absorbing agent) were referenced as comparative absorbent bodies (1), (2), (3), (4), (5), and (6). The simulated disposable diapers produced were referenced as comparative simulated disposable diapers (1), (2), (3), (4), (5), and (6).

Table 4 shows the results of measuring the absolute absorption amount (g) of each of the absorbent bodies (1) to (4) and comparative absorbent bodies (1) to (6) produced and of measuring liquid absorbing times (seconds) (at the first instance, the second instance, and the third instance), re-wet (g), and diffusion distance (%) of the simulated disposable diapers (1) to (4) and comparative simulated disposable diapers (1) to (6) produced.

TABLE 4

| | | | WA used | AA (g) | Liquid absorbing time (seconds) | | | Re-wet (g) | Diffusion distance (%) |
|---|---|---|---|---|---|---|---|---|---|
| | | | | | First instance | Second instance | Third instance | | |
| EX | 10 | AB 1 | WA 1 | 763 | 22 | 30 | 53 | 15 | 98 |
| | 11 | AB 2 | WA 2 | 755 | 23 | 35 | 61 | 14 | 98 |
| | 12 | AB 3 | WA 4 | 788 | 26 | 41 | 81 | 11 | 99 |
| | 13 | AB 4 | WA 6 | 742 | 14 | 27 | 50 | 17 | 99 |
| CEX | 18 | CAB 1 | CWA 1 | 752 | 23 | 50 | 97 | 18 | 91 |
| | 19 | CAB 2 | CWA 5 | 783 | 30 | 80 | 143 | 40 | 80 |
| | 20 | CAB 3 | CWA 7 | 750 | 27 | 62 | 112 | 21 | 85 |

TABLE 4-continued

|    | WA used | AA (g) | Liquid absorbing time (seconds) | | | Re-wet (g) | Diffusion distance (%) |
|----|---------|--------|---------|---------|---------|-----|-----|
|    |         |        | First instance | Second instance | Third instance | | |
| 21 | CAB 4   | CWA 8  | 743 | 24 | 48 | 93 | 23 | 82 |
| 22 | CAB 5   | CWA 10 | 712 | 12 | 25 | 48 | 53 | 99 |
| 23 | CAB 6   | CWA 12 | 758 | 24 | 45 | 85 | 29 | 92 |

"EX" stands for "Example".
"CEX" stands for "Comparative Example".
"WA" stands for "water absorbing agent".
"CWA" stands for "comparative water absorbing agent".
"AB" stands for "absorbent body".
"CAB" stands for "comparative absorbent body".
"AA" stands for "absolute absorption amount".

(Recap)

The evaluation results in Table 4 show that in comparison to the Comparative Examples, the particulate water absorbing agent of the present invention, when used in an absorbent body or simulated disposable diaper, not only maintains a sufficient absolute absorption amount (g) but also has liquid absorbing times (seconds) at the second instance and later which times are not significantly shorter than the liquid absorbing time (seconds) at the first instance. The evaluation results further show that the particulate water absorbing agent of the present invention also has a re-wet (g) smaller than those of the Comparative Examples and has a large diffusion distance (%). This indicates that the particulate water absorbing agent of the present invention has excellent physical properties.

More specifically, the comparative water absorbing agents 1, 5, 7, and 8 used in the respective comparative absorbent bodies 1-4 each had, for conventionally publicly known parameters such as the water absorption capacity (CRC), the swelling rate under load (AAP), and the particle size (%), values equivalent to those for the particulate water absorbing agent of the present invention. The comparative water absorbing agents 1, 5, 7, and 8 may, however, have a second-instance pure-water 50-fold swelling time (SST) of longer than 70 seconds (comparative absorbent bodies 1-3) or have a SST longer than the FST by longer than 10 seconds (comparative absorbent bodies 2-4). The comparative water absorbing agents 1, 5, 7, and 8 are thus insufficient in absorption when used in diapers (in particular, urination at the second instance and third instance of the multi-staged urination, and re-wet). This indicates that the SST of a particulate water absorbing agent is important when the particulate water absorbing agent is used in a diaper.

The comparative water absorbing agent 10 used in the comparative absorbent body 5 had a swelling rate under load (AAP) and particle size (%) (in other words, the particle size distribution (mass percentage of particles with particle diameters of 600 μm or larger) described above) equivalent to those of the particulate water absorbing agent of the present invention, and tended to have an SST and FST shorter than those of the particulate water absorbing agent of the present invention. The comparative water absorbing agent 10, however, had a low swelling rate CRC of 27 g/g relative to 0.9-mass % saline, and thus had an insufficient absolute absorption amount (g) when used in a diaper. In addition, the comparative water absorbing agent 10 had an extremely large re-wet (g) of 53 g, and is thus insufficient when used in a diaper. This indicates that it is important for a particulate water absorbing agent to have a particular CRC (32 g/g to 45 g/g) when the particulate water absorbing agent is used in a diaper.

The comparative water absorbing agent 12 used in the comparative absorbent body 6, which was different from the particulate water absorbing agent of the present invention only in the particle size and which had a conventionally typical particle size distribution (850-150 μm), was insufficient in absorption when used in a diaper (in particular, urination at the second instance and third instance of the multi-staged urination, and re-wet). This indicates that it is important for a water absorbing agent to have particular particle sizes (particles with sizes of 600 μm to 150 μm as defined through a standard-sieve classification account for 80 mass % or more) when used in a diaper.

TABLE 5

|     |    |        | Monomer concentration % | Internal crosslinking agent | | CRC (g/g) | AAP (g/g) | FST (sec) | SST (sec) | DST (sec) |
|-----|----|--------|-------|-------|-------|-----|-----|-----|-----|-----|
|     |    |        |       | Agent kind | AM (mol %) | | | | | |
| EX  | 1  | WA 1   | 33 | PEGDA | 0.045 | 34 | 29 | 67 | 62 | −5 |
|     | 2  | WA 2   | 43 | PEGDA | 0.047 | 34 | 30 | 61 | 58 | −3 |
| CEX | 14 | CWA 14 | 20 | PEGDA | 0.145 | 35 | 24 | 63 | 98 | 35 |
|     | 15 | CWA 15 | 25 | PEGDA | 0.105 | 36 | 23 | 69 | 83 | 14 |

"EX" stands for "Example".
"CEX" stands for "Comparative Example".
"WA" stands for "water absorbing agent".
"CWA" stands for "comparative water absorbing agent".
"AM" stands for "amount".

Table 5 shows, for the comparative water absorbing agent (14) and the comparative water absorbing agent (15), the concentration (mass %) of the monomer for production of the water absorbent resin particles, the kind and amount used (mol %) of the internal crosslinking agent, and the results of measurements of the CRC, AAP, FST, SST, and DST for comparison with the measurement results shown for the water absorbing agent (1) and water absorbing agent (2) in Tables 1 and 3.

The comparative water absorbing agent (14) and comparative water absorbing agent (15) had monomer concentrations lower than those of the water absorbing agent (1) and water absorbing agent (2), and thus each had a DST extremely longer than those of the water absorbing agent (1) and water absorbing agent (2).

TABLE 6

|     |    |        | 600 μm on amount (mass %) | 300 μm pass amount (mass %) | FST (seconds) | SST (seconds) | DST (seconds) |
|-----|----|--------|---------------------------|-----------------------------|---------------|---------------|---------------|
| EX  | 1  | WA 1   | 8                         | 26                          | 67            | 62            | −5            |
|     | 4  | WA 4   | 9                         | 21                          | 40            | 41            | 1             |
| CEX | 16 | CWA 16 | 0                         | 0                           | 91            | 91            | 0             |
|     | 17 | CWA 17 | 0                         | 0                           | 85            | 89            | 4             |

"EX" stands for "Example".
"CEX" stands for "Comparative Example".
"WA" stands for "water absorbing agent".
"CWA" stands for "comparative water absorbing agent".

Table 6 shows "300 μm pass amount (mass %)", which refers to the mass proportion, relative to the entire particulate water absorbing agent used, of the total amount of particles having passed through a JIS standard sieve having a mesh size of 300 μm described under [Particle size distribution (mass % of particles with sizes of 600 μm or larger as defined through a standard-sieve classification)] above. The phrase "600 μm on amount (mass %)" is as described above.

Neither of the comparative water absorbing agent (16) and comparative water absorbing agent (17) contained (i) particles with sizes of 600 μm or larger as defined through a standard-sieve classification or (ii) particles with sizes of 300 μm or less as defined through a standard-sieve classification. Thus, neither of the comparative water absorbing agent (16) and comparative water absorbing agent (17) contained fine particles. This is presumably why the comparative water absorbing agent (16) and comparative water absorbing agent (17) each had a long FST and a long SST.

INDUSTRIAL APPLICABILITY

The particulate water absorbing agent of the present invention and method for producing the particulate water absorbing agent, each of which involves using, as a parameter, a second-instance water absorbing speed (SST) (for a hydrogel swollen once to further absorb water), allow production of an absorbent body for a sanitary material such as a disposable diaper which absorbent body has excellent physical properties.

The invention claimed is:

1. A method for producing a particulate water absorbing agent, the particulate water absorbing agent being arranged such that particles having passed through a 150-μm mesh as defined through a standard-sieve classification are contained in an amount of 3 mass % or less, the method comprising the steps of:

(1) polymerizing a monomer aqueous solution including acrylic acid (salt) as a main component, the monomer aqueous solution having a monomer concentration of 30 mass % or more, the polymerization involving use of an internal crosslinking agent in an amount of 0.04 mol % or more and 0.07 mol % or less relative to the monomer and producing a hydrogel;

(2) drying the hydrogel, produced through the step (1), to produce a dried product having a swelling rate (CRC) of 35 g/g to 55 g/g;

(3) pulverizing the dried product into particles and optionally classifying the particles to produce a water absorbent resin powder including, at 80 mass % or more relative to the entire water absorbent resin powder, a particle having a size of 600 μm to 150 μm as defined through a standard-sieve classification;

(4) adding a surface-crosslinking agent, which includes a compound containing a hydroxyl group and/or a derivative group thereof, to the water absorbent resin powder, produced through the step (3), to decrease the swelling rate (CRC) by 3 g/g to 15 g/g to a swelling rate (CRC) of 32 g/g to 50 g/g to produce a surface-crosslinked water absorbent resin powder, and (5) adding a liquid permeability improving agent to the water absorbent resin powder simultaneously with and/or after the step (4).

2. The production method according to claim 1, wherein: the step (4) involves two or more kinds of organic compounds as the surface-crosslinking agent.

3. The production method according to claim 1, wherein: the step (5) involves adding, as the liquid permeability improving agent, a water-insoluble inorganic fine particle in an amount of 0.05 part by mass to 5.0 parts by mass relative to 100 parts by mass of the water absorbent resin powder and/or surface-crosslinked water absorbent resin powder, wherein the water-insoluble inorganic fine particles each have a particle size of 1 nm or higher and 50 μm or less.

4. The production method according to claim 3, wherein: the water-insoluble inorganic fine particle is made of silicon dioxide, wherein the water-insoluble inorganic fine particles each have a particle size of 1 nm or higher and 50 μm or less.

5. The production method according to claim 1, wherein:
the step (5) involves adding, as the liquid permeability improving agent, a water-soluble polyhydric metal cation in an amount of 0.01 part by mass to 5.0 parts by mass relative to 100 parts by mass of the water absorbent resin powder and/or surface-crosslinked water absorbent resin powder.

6. The production method according to claim 5, wherein:
the water-soluble polyhydric metal cation is an aluminum cation.

7. The production method according to claim 1, wherein:
the water absorbent resin powder to be subjected to the step (4) includes, at 5 mass % or less, a particle that passes through a 150-μm mesh as defined through a standard-sieve classification and/or includes, at 5 mass % or less, a particle that does not pass through a 710-μm mesh as defined through a standard-sieve classification.

8. The production method according to claim 1, wherein:
a first classification step is performed before the step (4); and
a second classification step is performed after the step (4).

* * * * *